United States Patent
Tatsumi et al.

(10) Patent No.: US 7,323,154 B2
(45) Date of Patent: Jan. 29, 2008

(54) TITANOSILICATE, PROCESS FOR ITS PRODUCTION, AND ITS USE IN PRODUCING OXIDIZED COMPOUND

(75) Inventors: Takashi Tatsumi, Kawasaki (JP); Peng Wu, Yokohama (JP); Katsuyuki Tsuji, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 482 days.

(21) Appl. No.: 10/506,336

(22) PCT Filed: Feb. 26, 2003

(86) PCT No.: PCT/JP03/02154

§ 371 (c)(1),
(2), (4) Date: Sep. 2, 2004

(87) PCT Pub. No.: WO03/074421

PCT Pub. Date: Sep. 12, 2003

(65) Prior Publication Data

US 2005/0209091 A1    Sep. 22, 2005

Related U.S. Application Data

(60) Provisional application No. 60/363,554, filed on Mar. 13, 2002.

(30) Foreign Application Priority Data

| Mar. 7, 2002 | (JP) | ................. 2002-061541 |
| Feb. 3, 2003 | (JP) | ................. 2003-026530 |
| Feb. 14, 2003 | (JP) | ................. 2003-036747 |

(51) Int. Cl.
*B01J 29/00* (2006.01)
*B01J 29/04* (2006.01)
*B01J 29/06* (2006.01)
*B01J 21/08* (2006.01)
*C01B 33/20* (2006.01)
*C01B 39/06* (2006.01)

(52) U.S. Cl. ............ 423/326; 423/702; 423/704; 423/705; 423/706; 423/713; 423/714; 423/718; 549/525; 549/529; 549/531; 502/242

(58) Field of Classification Search ............ 423/713, 423/326, 702, 704, 705, 706, 714, 718; 502/242; 549/525, 529, 531

See application file for complete search history.

(56) References Cited

U.S. PATENT DOCUMENTS 5,869,706 A    2/1999    Dartt et al.

(Continued)

FOREIGN PATENT DOCUMENTS

WO    WO 02 28774 A    4/2002

OTHER PUBLICATIONS

Wu P., et al.: "A Novel Titanosilicate with MWW Structure: II. Catalytic Properties in the Selective Oxidation of Alkenes" Journal of Catalysis, Academic Press, Duluth, MN, US, vol. 202, No. 2, Sep. 10, 2001, pp. 245-255.

(Continued)

*Primary Examiner*—David M Brunsman
(74) *Attorney, Agent, or Firm*—Sughrue Mion, PLLC

(57) ABSTRACT

A titanosilicate represented by the following compositional formula (1), wherein in the infrared absorption spectrum measured in the dehydrated state, the absorption spectrum has an absorption band having a relative maximum value at $930 \pm 15$ cm$^{-1}$:

$$xTiO_2 \cdot (1-x)SiO_2 \qquad \text{Compositional Formula (1)}$$

(wherein x is from 0.0001 to 0.2).

33 Claims, 13 Drawing Sheets

U.S. PATENT DOCUMENTS 6,114,551 A    9/2000   Levin et al.
6,387,349 B1 *  5/2002  Kulkarni et al. ............ 423/707
6,759,540 B2 *  7/2004  Oguchi et al. .............. 549/529
7,153,986 B2 * 12/2006  Abekawa et al. ........... 549/533

OTHER PUBLICATIONS

Wu P., et al.: A Novel Titanosilicate with MWW Structure: I. Hydrothermal Synthesis, Elimination of Extraframework Titanium, and Characterizations, J. Phys. Chem. B 2001, 105, 2897-2905.

* cited by examiner

TITANOSILICATE, PROCESS FOR ITS PRODUCTION, AND ITS USE IN PRODUCING OXIDIZED COMPOUND

This Application claims the priority of an application based on U.S. Application Ser. No. 60/363554 (filed on Mar. 13, 2002).

This application is a 371 of PCT/JP03/02 154, filed 26 Feb. 2003.

TECHNICAL FIELD

The present invention relates to a titanosilicate, a process for producing the titanosilicate, and a process for producing an oxidized compound using the titanosilicate.

More specifically, the present invention relates to a titanosilicate characterized in that in the infrared spectrum measured in the dehydrated state, the spectrum has an absorption band having a relative maximum value at $930\pm15$ cm$^{-1}$, and also relates to a process for producing the titanosilicate, and a process for producing an oxidized compound using the titanosilicate.

BACKGROUND ART

Generally, "zeolite" has been long a generic term of crystalline porous aluminosilicates and these are $(SiO_4)^{4-}$ and $(AlO_4)^{5-}$ having tetrahedral structures as the basic units of the structure. However, in recent years, it has been clarified that a structure peculiar or analogous to zeolite is present in other many oxides such as aluminophosphate.

International Zeolite Association (hereinafter simply referred to as "IZA") describes the definition of zeolite in *Atlas of Zeolite Structure Types*, 5th edition, edited by W. Meier, D. H. Meier, D. H. Olson and Ch. Baerlocher, Elsevier (2001) (Non-Patent Document 1) (hereinafter simply referred to as "Atlas"). According to this definition, substances other than aluminosilicate having a similar structure are dealt with as an objective substance of which structure is to be specified, and these are called a zeolite-like material.

The details of the history thereof are particularly described in Yoshio Ono and Tateaki Yajima (compilers), *Zeolite no Kagaku to Kogaku(Science and Engineering of Zeolite)*, pp. 1-13, published by Kodansha (Jul. 10, 2000) (Non-Patent Document 2).

The definition of "zeolite" as used in the present invention is based on the definition described in the above Yoshio Ono and Tateaki Yajima (compilers), *Zeolite no Kagaku to Kogaku(Science and Engineering of Zeolite)*, pp. 1-13, published by Kodansha (Jul. 10, 2000) where zeolite includes not only aluminosilicate but also those having an analogous structure, such as titanosilicate.

In the present invention, a structure code composed of three alphabetical capital letters derived from the names of standard substances initially used for the clarification of structure, approved by IZA, is used for the structure of zeolite. This includes those recorded in Atlas and those approved in the fifth and later editions.

Further, unless otherwise indicated specifically, the "aluminosilicate" and "titanosilicate" as used in the present invention are not limited at all on the difference such as crystalline/non-crystalline or porous/non-porous and include "aluminosilicates" and "titanosilicates" in all properties.

The "molecular sieve" as used in the present invention is a substance having an activity, operation or function of sieving molecules by the size and includes zeolite. This is described in detail in "Molecular Sieve" of *Hyojun Kagaku Yogo Jiten(Glossary for Standard Chemistry)*, compiled by Nippon Kagaku Kai, Maruzen (Mar. 30, 1991) (Non-Patent Document 3).

Recently, various studies have been made on the oxidation reaction of an organic compound using a titanosilicate, which is one of zeolites, as the catalyst and a peroxide as the oxidizing agent. Among titanosilicates, TS-1 as one of crystalline titanosilicates is used in various reactions after the synthesis method thereof is disclosed in U.S. Pat. No. 4,410,501 (Patent Document 1) and TS-1 is found to exhibit an activity in oxidation reactions using various peroxides. Specific examples thereof include a method disclosed in JP-B ("examined Japanese patent publication",)-4-5028 (Patent Document 2) where TS-1 is used as the catalyst in epoxidation of an olefin compound using hydrogen peroxide or an organic peroxide as the oxidizing agent.

The structure code of TS-1 is MFI similarly to ZSM-5 which is a representative synthetic zeolite, and has an oxygen 10-membered ring. On the infrared absorption spectrum of TS-1 measured in the dehydrated state, an absorption band having a relative maximum value at 960 cm$^{-1}$ is observed. The pore size is relatively small and 0.5 nm or less and therefore, the olefin compound which can be epoxidized is limited. Further, since the diffusion rate of the olefin compound as a reaction raw material into the inside of pores and the outflow rate of the product epoxy compound from pores are low, an industrially sufficient reaction activity can be hardly obtained. Moreover, a ring-opening reaction of the epoxy group takes place in the product epoxy compound, as a result, the selectivity disadvantageously decreases.

On the other hand, JP-A ("non-examined Japanese patent publication")-7-242649 (Patent Document 3) discloses a method of epoxidating an olefin compound using a crystalline titanium-containing molecular sieve having a structure similar to aluminum-free zeolite beta (structure code: *BEA) as the catalyst and using hydrogen peroxide or an organic peroxide as the oxidizing agent.

On the infrared absorption spectrum of a crystalline titanium-containing molecular sieve having a structure similar to aluminum-free zeolite beta measured in the dehydrated state, an absorption band having a relative maximum value at 960 cm$^{-1}$ is observed.

*BEA has a large pore size as compared with the structure code MFI of TS-1 and therefore, is expected to provide an effect of, for example, enabling a reaction of a compound having sterically high bulkiness or increasing the diffusion rate and thereby improving the reaction rate. Actually, the above-described patent publication discloses an example where a compound incapable of reacting by TS-1 can be oxidized. However, this oxidation reaction is disadvantageous in that the conversion of oxidizing agent is low in the case of using hydrogen peroxide as the oxidizing agent for the epoxidation reaction and since a ring-opening reaction of epoxide takes place to produce glycol, the selectivity decreases. Further, the molecular sieve described in that patent publication is high in the activity decreasing rate, in other words, short in the catalytic life and therefore, must be repeatedly subjected to a regeneration treatment on great occasions and this stands as a large obstacle to the implementation in an industrial scale.

On the other hand, in recent years, a synthetic zeolite having a structure code MWW different from MFI and *BEA is attracting an attention. The production process thereof is disclosed, for example, in JP-A-63-297210 (Patent Document 4).

Further, in Peng Wu, Takashi Tatsumi and Takayuki Komatsu, *Chemistry Letters*, 774 (2000) (Non-Patent Document 4), it is reported that a cyclohexene oxide can be produced by producing a crystalline titanosilicate containing a titanium atom in the crystal structure and having a structure code MWW and oxidizing cyclohexene using hydrogen peroxide and using the obtained crystalline titanosilicate as the catalyst. On the infrared absorption spectrum of the crystalline titanosilicate containing a titanium atom in the crystal structure and having a structure code MWW measured in the dehydrated state, an absorption band having a relative maximum value at 960 cm$^{-1}$ is observed.

However, the yield of the objective is not sufficiently high, both epoxide and diol are produced in a fairly large amount, failing in exhibiting a tendency of selectively giving either one compound, and therefore, this technique has a problem for industrial use.

As such, although various proposals have been made on the oxidation reaction of an olefin compound using a titanosilicate as the catalyst and a peroxide as the oxidizing agent, the technique practicable in industry is limited and the olefin compound to which any of these techniques can be applied is very limited. A technique industrially applicable to many olefin compounds is not yet found.

(Patent Document 1)
U.S. Pat. No. 4,410,501
(Patent Document 2)
JP-B-4-5028
(Patent Document 3)
JP-A-7-242649
(Patent Document 4)
JP-A-63-297210
(Non-Patent Document 1)
Atlas of Zeolite Structure Types, 5th edition edited by W. Meier, D. H. Meier, D. H. Olson and Ch. Baerlocher, Elsevier (2001)
(Non-Patent Document 2)
Yoshio Ono and Tateaki Yajima (compilers), Zeolite no Kagaku to Kogaku (Science and Engineering of Zeolite), published by Kodansha (Jul. 10, 2000)
(Non-Patent Document 3)
Hyojun Kagaku Yogo Jiten (Glossary for Standard Chemistry), compiled by Nippon Kagaku Kai, Maruzen (Mar. 30, 1991)
(Non-Patent Document 4)
Peng Wu, Takashi Tatsumi and Takayuki Komatsu, *Chemistry Letters*, 774 (2000)

DISCLOSURE OF INVENTION

An object of the present invention is to provide a titanosilicate usable as a catalyst in an oxidation reaction, a process for producing the titanosilicate, and a process for producing an oxidized compound by an oxidation reaction using the titanosilicate.

As a result of earnest study, the present inventors have found that a titanosilicate having an infrared absorption spectrum measured in the dehydrated state such that the absorption spectrum has an absorption band having a relative maximum value at 930±15 cm$^{-1}$ acts effectively as the catalyst in an oxidation reaction and provides an intended oxidized compound with high selectivity. The present invention has been accomplished based on this discovery.

More specifically, the present invention (I) is a titanosilicate represented by the following compositional formula (1), wherein in the infrared absorption spectrum measured in the dehydrated state, the absorption spectrum has an absorption band having a relative maximum value at 930±15 cm$^{-1}$:

$$xTiO_2 \cdot (1-x)SiO_2 \qquad \text{Compositional Formula (1)}$$

(wherein x is from 0.0001 to 0.2).

The present invention (II) is a process for producing the titanosilicate of the present invention (I).

Further, the present invention (III) is a process for producing an oxidized compound, wherein an oxidation reaction of an organic compound is performed using an oxidizing agent in the presence of the titanosilicate of the present invention (I).

The present invention comprises, for example, the following matters.

[1] A titanosilicate represented by the following compositional formula (1), wherein in the infrared absorption spectrum measured in the dehydrated state, the absorption spectrum has an absorption band having a relative maximum value at 930±15 cm$^{-1}$:

$$xTiO_2 \cdot (1-x)SiO_2 \qquad \text{Compositional Formula (1)}$$

(wherein x is from 0.0001 to 0.2).

[2] The titanosilicate according to [1], wherein in the infrared absorption spectrum measured in the dehydrated state, the greatest value in the region of 900-950 cm$^{-1}$ of the absorption spectrum is present in the region of 930±15 cm$^{-1}$.

[3] The titanosilicate according to [2], wherein in the infrared absorption spectrum measured in the dehydrated state, the greatest value in the region of 900-950 cm$^{-1}$ of the absorption spectrum is present in the region of 930±10 cm$^{-1}$.

[4] The titanosilicate according to any one of claims [1]-[3], wherein in the infrared absorption spectrum measured in the dehydrated state, the absorption spectrum has an absorption band having a relative maximum value at 1010±15 cm$^{-1}$ in addition to 930±15 cm$^{-1}$.

[5] The titanosilicate according to any one of [1]-[4], wherein in the infrared absorption spectrum-measured in the dehydrated state, the absorption spectrum has an absorption band having a relative maximum value at 865±15 cm$^{-1}$ in addition to 930±15 cm$^1$.

[6] The titanosilicate according to any one of [1]-[5], which is a crystalline titanosilicate having a structure code MWW characterized by the powder X-ray diffraction pattern shown in Table 1:

TABLE 1

| Powder X-Ray Diffraction Lines Provided by MWW Structure | |
|---|---|
| d/Å | Relative Intensity (s: strong, m: medium, w: weak) |
| 12.3 ± 0.6 | s |
| 11.0 ± 0.6 | s |
| 8.8 ± 0.5 | s |
| 6.2 ± 0.4 | m |
| 5.5 ± 0.3 | w |
| 3.9 ± 0.2 | m |
| 3.7 ± 0.2 | w |
| 3.4 ± 0.2 | s |

(in the above Table, "d/Å" means that the unit of the lattice spacing d is Angstrom.)

[7] The titanosilicate according to any one of [1] to [7], wherein x is from 0.001 to 0.2.

[8] A process for producing the titanosilicate described in any one of [1] to [7], comprising the following first to fourth steps:

First Step:
   a step of heating a mixture containing a template compound, a boron-containing compound, a silicon-containing compound and water to obtain a precursor (A);

Second Step:
   a step of acid-treating the precursor (A) obtained in the first step;

Third Step:
   a step of heating the acid-treated precursor (A) obtained in the second step together with a mixture containing a template compound, a titanium-containing compound and water to obtain a precursor (B); and Fourth Step:
   a step of calcining the precursor (B) obtained in the third step to obtain the titanosilicate.

[9] The process for producing the titanosilicate according to [8], wherein the following first-2 step is performed between the first step and the second step and the substance obtained in the first-2 step is used instead of the precursor (A) in the second step:

First-2 Step:
   a step of calcining a part or entirety of the precursor (A) obtained in the first step.

[10] The process for producing the titanosilicate according to [8 or 9], wherein the following third-2 step is performed between the third step and the fourth step and the substance obtained in the third-2 step is used instead of the precursor (B) in the fourth step:

Third-2 Step:
   a step of acid-treating a part or entirety of the precursor (B) obtained in the third step.

[11] The process for producing the titanosilicate according to any one of [8]-[10], wherein the following third-3 step is performed between the third step or third-2 step, and the fourth step, and the substance obtained in the third-3 step is used instead of the precursor (B) in the fourth step:

Third-3 Step:
   a step of heating the precursor (B) obtained in the third step, or the acid-treated precursor (B) obtained in the third-2 step, in the presence of a swelling agent so as to swell the layered precursor, to thereby modify the state of the superposition thereof.

[12] The process for producing the titanosilicate according to any one of [8] to [11], wherein the template compound is a nitrogen-containing compound.

[13] The process for producing the titanosilicate according to [12], wherein the nitrogen-containing compound is amine and/or quaternary ammonium compound.

[14] The process for producing the zeolite substance according to [12], wherein the nitrogen-containing compound is at least one member selected from the group consisting of piperidine, hexamethyleneimine and a mixture thereof.

[15] The process for producing the titanosilicate according to any one of [8] to [14], wherein the boron-containing compound is at least one member selected from the group consisting of boric acid, borate, boron oxide, boron halide and trialkylborons.

[16] The process for producing the titanosilicate according to any one of [8] to [15], wherein the silicon-containing compound is at least one member selected from the group consisting of silicic acid, silicate, silicon oxide, silicon halide, fumed silicas, tetraalkyl orthosilicates and colloidal silica.

[17] The process for producing the titanosilicate according to any one of [8] to [16], wherein the ratio of boron to silicon in the mixture at the first step is, in terms of the molar ratio, boron:silicon=0.01 to 10:1.

[18] The process for producing the titanosilicate according to any one of [8] to [17], wherein the ratio of boron to silicon in the mixture at the first step is, in terms of the molar ratio, boron:silicon=0.05 to 10:1.

[19] The process for producing the titanosilicate according to any one of [8] to [18], wherein the ratio of water to silicon in the mixture at the first step is, in terms of the molar ratio: water:silicon=5 to 200:1.

[20] The process for producing the titanosilicate according to any one of [8] to [19], wherein the ratio of template compound to silicon in the mixture at the first step is, in terms of the molar ratio, template compound:silicon=0.1 to 5:1.

[21] The process for producing the titanosilicate according to any one of [8] to [19], wherein the heating temperature in the first step is from 110 to 200° C.

[22] The process for producing the titanosilicate according to any one of [8] to [20], wherein the acid used for the acid-treatment in the second step is a nitric acid or a sulfuric acid.

[23] The process for producing the titanosilicate according to any one of [8] to [22], wherein the heating temperature in the third step is from 110 to 200° C.

[24] The process for producing the titanosilicate according to any one of [8] to [23], wherein the calcination temperature in the fourth step is from 200 to 700° C.

[25] The process for producing the titanosilicate according to any one of [9] to [24], wherein the calcination temperature in the first-2 step is from 200 to 700° C.

[26] The process for producing the titanosilicate according to any one of [8] to [25], wherein in the third step, the acid-treated precursor (A) obtained in the second step and the mixture containing a template compound, a titanium-containing compound and water are previously mixed and then heated.

[27] The process for producing the titanosilicate according to any one of [8] to [26], wherein in the third step, the acid-treated precursor (A) is treated by a dry gel method such that a mixture containing the acid-treated precursor (A) obtained in the second step, a titanium-containing compound and water and a mixture containing a template compound and water are charged separately, the vapor of the containing a template compound and water is caused to contact the mixture containing the titanium-containing compound and the (acid-treated) precursor (A).

[28] A process for producing an oxidized compound, comprising performing an oxidation reaction of an organic compound using the oxidizing agent in the presence of the titanosilicate described in any one of [1] to [7].

[29] The process for producing an oxidized compound according to [28], wherein the oxidizing agent is oxygen or peroxide.

[30] The process for producing an oxidized compound according to [29], wherein the peroxide is at least one compound selected from the group consisting of hydrogen peroxide, tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, ethylnaphthalene hydroperoxide and peracetic acid.

[31] The process for producing an oxidized compound according to any one of [26] to [30], wherein the oxidation reaction is performed in the presence of at least one solvent selected from the group consisting of alcohols, ketones, nitriles and water.

[32] The process for producing an oxidized compound according to any one of [26] to [32 wherein the oxidation reaction of an organic compound is an oxidation reaction of a carbon-carbon double bond.

[33] The process for producing an oxidized compound according to any one of [26] to [32], wherein the oxidation reaction of an organic compound is an epoxidation reaction or a diolation reaction.

[34] The process for producing an oxidized compound according to any one of [26] to [31], wherein the oxidation reaction of an organic compound is an ammoximation.

BEST MODE FOR CARRYING OUT THE INVENTION

Figure 1:
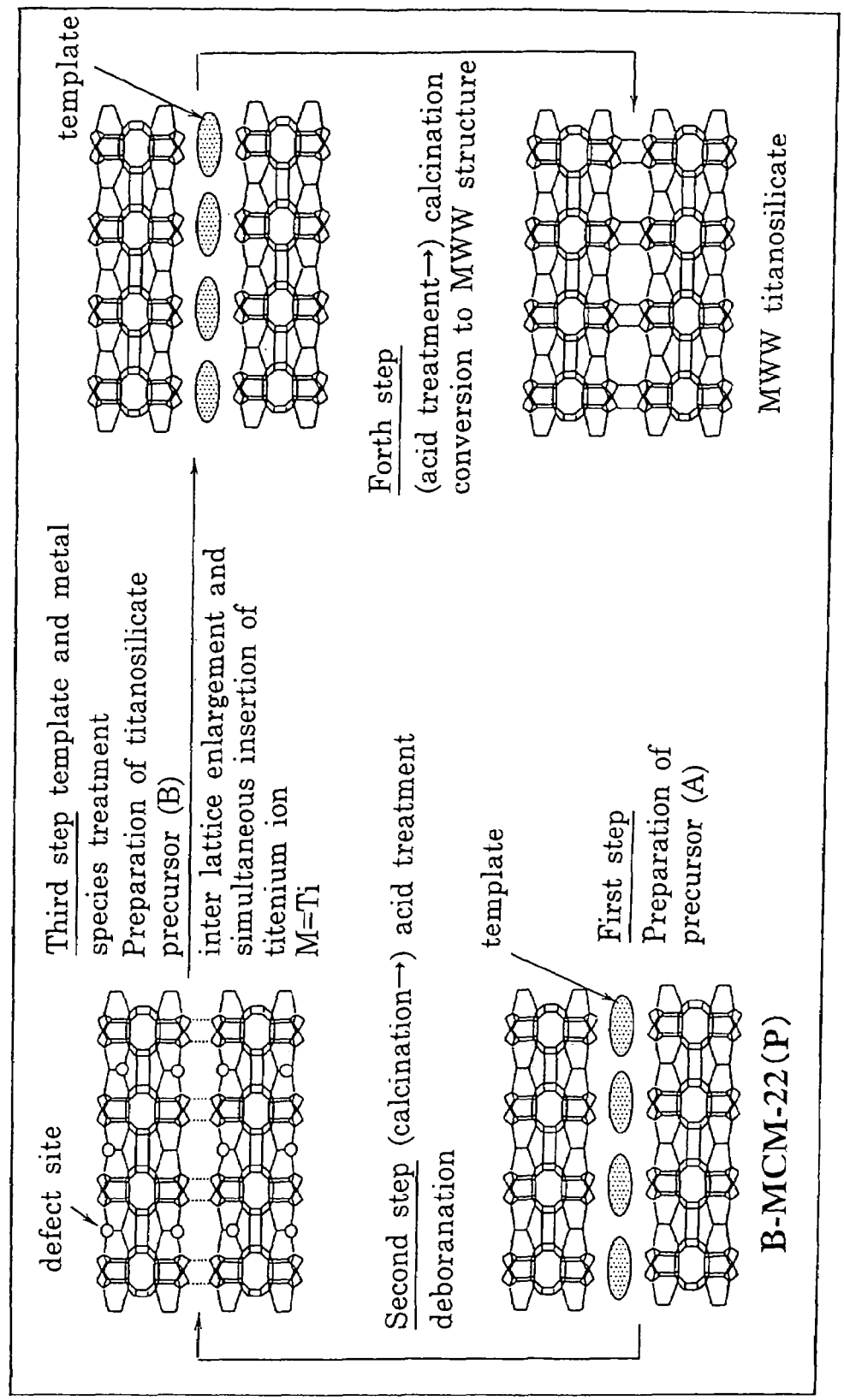
FIG. 1 is a schematic view for illustrating a process for producing a titanosilicate substance by a post-synthesis process.

Hereinbelow, the present invention will be described in detail with reference to the accompanying drawings as desired. In the following description, "%" and "part(s)" representing a quantitative proportion or ratio are those based on mass, unless otherwise noted specifically.

(Present invention (I))

The present invention (I) is first described. The present invention (I) is a titanosilicate represented by the following compositional formula (1), wherein in the infrared absorption spectrum measured in the dehydrated state, the absorption spectrum has an absorption band having a relative (or local) maximum value at $930\pm15$ cm$^{-1}$:

$$xTiO_2.(1-X)SiO_2 \qquad \text{Compositional Formula (1)}$$

(wherein x is from 0.0001 to 0.2).

The titanosilicate of the present invention has an infrared absorption spectrum measured in the dehydrated state, where the spectrum has an absorption band having a relative maximum value at $930\pm15$ cm$^{-1}$. However, the absorption band having a relative maximum value is not limited thereto and an absorption band having a relative maximum value also at $860\pm15$ cm$^{-1}$ or $1,010\pm15$ cm$^{-1}$ may also be present. Also, an absorption band having a relative maximum value at 960 cm$^{-1}$ as seen in general titanosilicates can also be present in combination. More preferably it is preferred that, in the infrared absorption spectrum measured in the dehydrated state, the greatest (or maximum) value in the region of 900-950 cm$^{-1}$ of the absorption spectrum is present in the range of $930\pm15$ cm$^{-1}$ (more preferably, in the range of $930\pm10$ cm$^{-1}$); and that the area of the absorption band having the relative maximum valve at $930\pm15$ cm$^{-1}$ is larger than that of the absorption band having the relative maximum value at 960 cm$^{-1}$.

Herein, in the present invention, the infrared absorption spectrum to be measured is characterized by an absorption spectrum wherein the absorbance corresponds to the ordinate axis, and the wave number corresponds to the abscissa axis. It is also possible to discuss the characteristic of the spectrum by using an absorption spectrum wherein the transmittance corresponds to the ordinate axis. However, in the present invention, the characteristic of the spectrum is prescribed by using the absorption spectrum, since the characteristic can be described clearly when the measured values are converted into the absorbance.

In the present invention, of course, the "absorption band having a relative maximum value" includes an absorption band having a relative maximum value in the spectrum. However, in the present invention, the "absorption band having a relative maximum value" also includes a case (such as shoulder peak) wherein an absorption band is present reasonably or definitely in a position of interest.

This treatment is based on the following reasons. That is, in the case of silicate compounds, there is present a very strong absorption band due to Si—O—Si in a region of 1010-1250 cm$^{-1}$, and an absorption band present in a region of 900-1000 cm$^{-1}$ is inevitably affected by this large absorption band to a certain extent. Therefore, when the sample to be measured has a very high concentration, or the measurement conditions are not appropriate, it is not rare that, although there is inherently an absorption band at a predetermined position, the corresponding maximum value is not practically recognized, and only a shoulder peak is recognized (or even a shoulder peak is not practically recognized). At first, it is preferred to select the measurement conditions as described hereinafter, so as to provide good results, but there is a case wherein the method of detecting the relative maximum value should be devised.

There is a method of detecting the relative maximum value wherein a first differential curve of the absorption spectrum and/or a second differential curve thereof is determined. When there is a clear relative maximum value in the a source or original spectrum, the first differential curve thereof should cross the 0 (zero) point of the ordinate axis, and this point corresponds to the wave number providing the relative maximum value. On the other hand, even when here is no clear relative maximum value in a source spectrum, there will be two inflection points before and after the point at which the wave number providing the relative maximum value is to be present. Accordingly, in such a case, it can be considered that there is a relative maximum value between two points at which the second differential curve cross the zero point of the ordinate axis. When the shape of a curve between the two points is near to bilateral symmetry, it is possible to consider for convenience, that the wave number corresponding to the local minimum of the second differential curve is treated as the wave number at which there is inherently present the relative maximum value in the source spectrum.

Further, it is also possible to discuss the presence and relative maximum value of divided peaks by deconvoluting (or splitting) peaks with a commercially available software for deconvoluting peaks (However, when such a commercially available software is used, in some cases, there is the possibility of arbitrarily resolving the peak).

The term "dehydrated state" as used in the present invention means that water adsorbed to the substance to be measured, which becomes an interfering substance at the measurement of the infrared absorption spectrum in the vicinity of 800 to 1,200 $cm^{-1}$, is removed and a measurable state of an intended absorption band is provided. In general, if the titanosilicate of the present invention is in the state where adsorbed water is present, even when the absorption spectrum in the above-described specific measurement region is measured, a peak with a relative maximum value of $930 \pm 15$ $cm^{-1}$, $865 \pm 15$ $cm^{-1}$ or $1,010 \pm 15$ $cm^{-2}$ is not observed on the spectrum. This is considered to result because the oscillation showing the peak is inhibited by the adsorbed water. Accordingly, in order to confirm such a peak, adsorbed water must be removed. Here, the absolute amount of adsorbed water on the substance to be measured is not a problem and it is sufficient if a state of enabling the measurement of the infrared absorption spectrum in that region is provided.

Usually, the "dehydrated state" as used herein can be attained by a treatment for about 1 hour while heating at 500° C. under a pressure of $10^{-3}$ Pa. More specifically, this state can be realized by adding an appropriate amount of potassium bromide to a titanosilicate sample, forming the mixture into pellets, setting the pellets in a quartz-made cell, and heating and thereby degassing the cell for 1 hour at 500° C. under a pressure of $10^{-3}$ Pa.

When the dilution of a sample is insufficient, there is a possibility that the above-mentioned absorption of Si—O—Si becomes very large, and an absorption of interest having a wave number lower than 1010 $cm^{-1}$ is superposed on the tail of the large peak, and as a result, such an absorption of interest cannot be observed. Therefore, the dilution ratio may preferably be, in terms of the weight ratio of the sample and potassium bromide, in the range of sample:potassium bromide=0.001-0.05. It is necessary to pay attention to the preparation of a pellet, since the quality of the resultant spectrum can be lowered when a part of the pellet is damaged. Further, it is necessary to adopt an apparatus for measuring infrared absorption spectra and measurement conditions which can sufficiently detect an absorption band of interest. Transmission method is preferred as the measuring method. A diffuse reflection method can also be used, but in this case, it is necessary to adopt a method capable of detecting a minute absorption band, e.g., by modifying the spectrum by a Kubelka-Munk method. It is at least necessary to use a Fourier transformation type apparatus. Further, the measurement should be conducted under a condition corresponding to a resolution of 4 $cm^{-1}$ or less, more preferably 2 $cm^{-1}$ or less.

In the titanosilicate of the present invention (1), the ratio of $TiO_2$ and $SiO_2$ present as constituent units can be specified by the molar ratio. Accordingly, x means the molar ratio of $TiO_2$ present in the titanosilicate and (1-x) is the molar ratio of $SiO_2$ present. In other words, x/(1-x) merely shows the molar ratio of titanium/silicon and does not deny the presence of other elements in the titanosilicate.

In compositional formula (1), x is from 0.0001 to 0.2, preferably from 0.001-0.2, more preferably from 0.005 to 0.2, most preferably from 0.01 to 0.1. Other than titanium introduced into the framework (or skeleton) by substituting to silicon, titanium species present in the site out of the crystal framework, for example, 6-coordination titanium species or anatase-like titanium oxide may coexist, however, these titanium species outside the framework generally accelerate the side reaction or narrow the pore to inhibit the diffusion of reactant and therefore, the amount of these species present may preferably be small.

In compositional formula (1), the specified x is assumed to be the ratio of silicon contained inside the framework, however, in the case where titanium is present outside the framework in addition to titanium inside the framework, it is actually difficult to precisely determine the titanium contained inside the framework. Generally, for example, on the ultraviolet-visible absorption spectrum, the absorption in the vicinity of 210 nm is assigned to titanium inside the framework, the absorption in the vicinity of 260 nm is assigned to 6-coordination titanium species outside the framework, and the absorption in the vicinity of 330 nm is assigned to anatase-like titanium species. Accordingly, when an absorption is present in the vicinity of 210 nm, it is known that the titanosilicate contains titanium inside the framework. In fact, the titanosilicate of the present invention (I) has an absorption in the vicinity of 220 nm and this reveals that titanium is present inside the framework. However, when an absorption is present at other wavelengths, the ratio of these titanium species present cannot be quantitatively discussed even by combining it with other means such as nuclear magnetic resonance method or infrared absorption method.

Clearly known is only that the value in the molar ratio of titanium to silicon calculated from the proportions of titanium and silicon obtained after the composition analysis by elementary analysis or the like is the relative maximum value of the amount of titanium contained inside the framework. As described above, the molar ratio of titanium contained inside the framework is difficult to directly determine. In the present invention, for the convenience's sake, the molar ratio of titanium and silicon calculated as x in compositional formula (1) by the analysis of composition is used as the molar ratio of titanium contained inside the framework.

The titanosilicate of the present invention (I) where silicon is substituted by titanium may contain other elements in addition to titanium, silicon and oxygen insofar as these elements do not so much adversely affect the reactivity of titanosilicate. Particularly, in the case of producing the titanium silicate of the present invention (I) by the production process using boron as the structure supporting agent, which is described later, a very small amount of boron may remain even if an operation of removing boron is performed. However, a very small amount of boron does not so much adversely affect the reactivity of titanosilicate and therefore, may be substantially present. In principle, other trivalent metals such as aluminum, gallium, iron and chromium can also be used as the structure supporting agent in place of boron and if the case is so, a very small amount of such an element sometimes remains inside and outside the framework.

As used in the synthesis of MCM-22, alkali metals such as sodium and potassium are generally expected to act as a mineralizer and therefore, can also be used for the purpose of accelerating the crystallization at the production of titanosilicate of the present invention (I). However, in general, alkali metals inhibit the catalytic function of crystalline titanosilicate and are preferably removed by ion exchanging, acid treatment, or the like.

The structure code MWW is one of known molecular sieve structures and is greatly characterized by having a pore composed of an oxygen 10-membered ring, and a super cage (0.7×0.7×1.8 nm). Details on the structure are described, for example, in Atlas, 5th ed. or can be read on the internet, the homepage of IZA Structure Commission (http://www.iza-structure.org/) (as of February, 2002). Known examples of the molecular sieve having this structure include MCM-22 (*Science*, Vol. 264, 1910 (1994)), SSZ-25 (European Patent 231860), ITQ-1 (*Chem. Mater.*, Vol. 8, 2415 (1996) and *J. Phys. Chem. B*, Vol. 102, 44 (1998)), ERB-1 (European Patent 203032) and PSH-3 (U.S. Pat. No. 449,409). The molecular sieve having the structure code MWW can be identified by its characteristic pattern on the X-ray diffraction (hereinafter simply referred to as "XRD"). As for the XRD pattern, for example, a simulation pattern of ITQ-1 can be available on the above-described homepage. Representative diffraction pattern is shown in the following Table 2.

TABLE 2

Powder X-Ray Diffraction Lines Provided by MWW Structure

| d/Å | Relative Intensity (s: strong, m: medium, w: weak) |
| --- | --- |
| 12.3 ± 0.6 | s |
| 11.0 ± 0.6 | s |
| 8.8 ± 0.5 | s |
| 6.2 ± 0.4 | m |
| 5.5 ± 0.3 | w |
| 3.9 ± 0.2 | m |
| 3.7 ± 0.2 | w |
| 3.4 ± 0.2 | s |

The present invention (II) is described below. The present invention (II) is a process for producing the titanosilicate, comprising the following first to fourth steps:

First Step:
a step of heating a mixture containing a template compound, a boron-containing compound, a silicon-containing compound and water to obtain a precursor (A);

Second Step:
a step of acid-treating the precursor (A) obtained in the first step;

Third Step:
a step of heating the acid-treated precursor (A) obtained in the second step together with a mixture containing a template compound, a titanium-containing compound and water to obtain a precursor (B); and Fourth Step:
a step of calcining the precursor (B) obtained in the third step to obtain the titanosilicate.

Crystalline MWW-type titanosilicates in general can be synthesized by a conventionally known direct synthesis method or a post synthesis method such as atom planting. In the synthesis by atom planting, for example, a molecular sieve having an MWW structure containing boron or aluminum is first synthesized, then at least a part of boron or aluminum is removed by a water vapor treatment, and the residue is contacted with a titanium compound such as titanium tetrachloride.

On the other hand, the titanosilicate of the present invention can be produced only by the production process of the present invention (II) so far. The production process of titanosilicate of the present invention (II) is characterized in that the step of producing the titanosilicate comprises four steps, that is, a step of heating a mixture containing a template compound, a boron-containing compound, a silicon-containing compound and water to obtain a precursor (A); a step of acid-treating the obtained precursor (A); a step of heating the obtained acid-treated precursor (A) together with a mixture containing a template compound, a titanium-containing compound and water to obtain a precursor (B); and a step of finally calcining the obtained precursor (B) to produce the titanosilicate. Of course, a step other than these may be provided between respective steps.

The first step is described below. The first step in the production process of titanosilicate of the present invention (II) is a step of heating a mixture containing a template compound, a boron-containing compound, a silicon-containing compound and water to obtain a precursor (A).

The "template compound" used here is a compound having an activity of specifying the structure, particularly the pore shape at the synthesis of a zeolite having an MWW structure. This compound is not particularly limited as long as it can be removed later by calcination. Examples thereof generally include a nitrogen-containing compound, and preferably amine and/or quaternary ammonium compound. Specific examples thereof include piperidine, hexamethyleneimine and/or a mixture thereof, however, the present invention is not limited thereto.

The boron compound which can be used in the first step is not particularly limited. Preferred specific examples thereof include boric acid, however, this can be used also in the form of a borate such as sodium borate.

The silicon-containing compound which can be used in the first step is not particularly limited and specific examples thereof include silicic acid, silicate, silicon oxide, silicon halide, fumed silicas, tetraalkyl orthosilicates and colloidal silica. In any case, a high-purity compound is preferred but particularly in the case of colloidal silica, a colloidal silica having a small alkali content is preferred.

The ratio of boron to silicon in the mixture used in the first step may preferably be, in terms of the molar ratio, boron:silicon=0.01 to 10:1, more preferably boron:silicon=0.05 to 5:1, still more preferably boron:silicon=0.3 to 3:1. As described hereinbelow, when the precursor (A) is to be synthesized under an alkali metal-free condition, the use of a large amount of boron is necessary. In such a case, it is preferred that boron:silicon=0.3 to 2:1, more preferably boron:silicon=1 to 2:1.

The ratio of water to silicon in the mixture used in the first step may preferably be, in terms of the molar ratio, water:silicon=5 to 200:1, more preferably water:silicon=15 to 50:1.

The ratio of the template compound to silicon in the mixture used in the first step may preferably be, in terms of the molar ratio, template compound:silicon=0.1 to 5:1, more preferably template compound:silicon=0.3 to 3:1, still more preferably template compound:silicon=0.5 to 2:1.

Further, it is also useful to add a seed crystal in addition to these raw materials. In this case, it is sometimes possible to expect an effect of shortening the crystallization time or providing a product having a small particle size. As the seed crystal, it is preferred to use a substance having an MWW structure or a structure similar to MWW such as precursor therefor having a layered structure (e.g., MCM-22 (P)), which has preliminarily been synthesized. It is particularly preferred to use a layered-structure precursor for an MWW type zeolite substance containing boron. For example, it is possible to add a part of a precursor (A) obtained in the past first step, to a mixture to be used in the first step as the seed crystal. The timing for the addition thereof is not particularly limited, but it is possible that all the other raw materials are mixed, the seed crystal is added to the resultant mixture, and thereafter the mixture is stirred and then heated. As the amount of the seed crystal to be added, the molar ratio of silicon contained in the seed crystal to the silicon in the silicon-containing compound to be used as main raw material may preferably be a ratio of seed crystal:main raw material=0.0001-0.2:1, more preferably 0.001-0.05:1. If the addition amount is to small, it is difficult to obtain the above-mentioned effect. If the addition amount is to large, the productivity will become lower.

It is possible to add a compound including an alkali metal such as sodium or potassium, and in such a case the crystallization time can sometimes be shortened. In general, the presence of alkali metal can provide a tendency such that it can inhibit the introduction of an element other than boron, aluminum, and silicon into the framework of a zeolite substance, or it can promote the reaction of a compound including titanium in itself to form titania or similar compound. It is a well-known fact that titanium does not enter the zeolite framework in a good manner, if an alkali metal is present in the system in the case of synthesis of titanosilicate such as TS-1, and the added titanium source is incorporated the product as titania or the species similar to titania. However, in the present invention, even when an alkali metal is used in the first step, it is also possible to substantially remove the alkali metal in the acid treatment (second step), prior to the step of introducing the metal species into the framework (third step). Accordingly, it is also possible to use an alkali metal in the first step of this invention, and it is possible that an alkali metal is present in a molar ratio of alkali metal:silicon:=0.0001-0.2:1, more preferably about 0.001-0.1:1. As the alkali metal source, there are hydroxides, nitric acid salts, chlorides, sulfuric acid salts, salt of other metal acid, but a hydroxide or borate may most preferably be used.

The heating temperature in the first step is not particularly limited. However, in the case of synthesizing a precursor (A), this may preferably be performed under the hydrothermal reaction conditions. The term "hydrothermal reaction" as used herein means, as described in "Hydrothermal Reaction" of *Hyojun Kagaku Yogo Jiten(Glossary for Standard Chemistry)*, compiled by Nippon Kagaku Kai, Maruzen (Mar. 30, 1991), a synthesis or modification reaction performed in the presence of high-temperature water, particularly high-temperature high-pressure water. In particular, a synthesis reaction using the hydrothermal reaction is referred to as "hydrothermal synthesis". Accordingly, the heating in the first step may preferably be performed by placing a mixture containing a template compound, a boron-containing compound, a silicon-containing compound and water in a closed container such as autoclave, under hydrothermal synthesis conditions of applying a pressure while heating. The temperature may preferably be from 110 to 200° C., more preferably from 120 to 190° C.

If the temperature in the hydrothermal synthesis is less than this range, the intended product may not be obtained or even if obtained, the heating may take a long time and this is not practical. On the other hand, if the temperature exceeds this range, the purity of the finally obtained titanosilicate disadvantageously decreases.

The hydrothermal synthesis is usually used for a time period of 2 hours to 30 days. The hydrothermal synthesis time may preferably be from 3 hours to 10 days. If the hydrothermal synthesis time is less than this range, crystallization may proceed insufficiently to fail in obtaining a high-performance precursor (A). On the other hand, even if the hydrothermal synthesis is performed for a time period exceeding this range, the performance of the precursor (A) is not substantially enhanced but rather adverse effects may be caused such as conversion into other phase or increase of the particle size and this it not preferred.

The second step is described below. The second step is a step of acid-treating the precursor (A) obtained in the first step or first-2 step to obtain a deboronated silicate.

The precursor (A) obtained in the first step may be subjected as it is to the acid treatment but when the precursor is calcined (first-2 step) before the acid treatment and thereafter acid-treated, boron inside the framework can be more efficiently removed. Hereinbelow, the precursors (A) obtained in the first step and first-2 step are inclusively referred to as "precursor (A)".

The term "acid treatment" as used herein means contacting with an acid, more specifically, to contact a solution containing an acid, or an acid itself with the precursor (A) obtained in the first step. The contacting method is not particularly limited and a method of spraying or coating an acid or an acid solution on the precursor (A) or a method of dipping the precursor (A) in an acid or an acid solution may be used. The method of dipping the precursor (A) in an acid or an acid solution is preferred because this method is simple and easy.

The acid used for this step may be an inorganic acid, an organic acid or a salt thereof. Specific preferred examples of the inorganic acid include a hydrochloric acid, a sulfuric acid, a nitric acid and a phosphoric acid. Specific preferred examples of the organic acid include a formic acid, an acetic acid, a propionic acid and a tartaric acid. Examples of the salt thereof include an ammonium salt.

In the case of using the acid as a solution, the solvent therefor is not particularly limited. Specific examples of the solvent include water, alcohols, ethers, esters and ketones. Among these, water is suitable.

The acid concentration is also not particularly limited but the acid is suitably used in a concentration of 0.1 to 10 mol/liter. The treatment may be performed at a temperature of 0 to 200° C. but may preferably be performed at 50 to 180° C., more preferably from 60 to 150° C. The treatment time is from 0.1 hour to 3 days, preferably from 2 hours to 1 day.

It is also possible to conduct the cycle of (the first-2 step→second step) plural times, in order to minimize the residual content of boron.

The third step is described below. The third step is a step of heating the deboronated silicate obtained in the second step together with a mixture containing a template compound, a titanium-containing compound and water to obtain a precursor (B).

The "template compound" as used herein is, similarly to that used in the first step, a compound having an activity of specifying the structure, and/or pore shape at the synthesis of a zeolite having an MWW structure. This compound is not particularly limited as long as it can be removed later by calcination. Examples thereof generally include a nitrogen-containing compound and specific examples thereof include piperidine, hexamethyleneimine and/or a mixture thereof, however, the present invention is not limited thereto.

The template compound used in the third step may be the same as or different from the template compound used in the first step.

The titanium-containing compound which can be used in the third step is not particularly limited. Specific examples of the titanium-containing compound include titanium oxide, titanium halide and tetraalkyl orthotitanates, however, the present invention is not limited thereto. Among these, titanium halide and tetraalkyl orthotitanates are preferred in view of easy and simple handleability. Specific suitable examples thereof include titanium tetrafluoride, tetraethyl orthotitanate, tetrapropyl orthotitanate and tetrabutyl orthotitanate. A water-soluble titanium peroxide which is provided by reacting a titanium compound and hydrogen peroxide is an example of the preferred compound.

The precursor (B) obtained in the third step can be synthesized by previously mixing all of the acid-treated precursor (A) obtained in the second step, a template compound, a titanium-containing compound and water and heating the mixture to perform a so-called hydrothermal synthesis similarly to the first step.

The order of mixing is not particularly limited. For example, in order to homogenize the raw material composition, it is preferred that at first, a mixture liquid comprising water, a template compound, and element-containing compound is prepared, and the acid treated precursor (A) provided in the second step is added to the resultant mixture. Further, the mixture liquid comprising water, a template compound, and the element-containing compound may preferably be a uniform solution rather than slurry, and it is desirable to devise the kind and concentration of the element-containing compound or mixing condition (temperature, time) so as to achieve such a solution.

The ratio of titanium in the mixture to silicon in the acid-treated precursor used in the third step may preferably be, in terms of the molar ratio, titanium:silicon=0.001 to 0.3:1, more preferably titanium:silicon=0.005 to 0.2 1, still more preferably titanium:silicon=0.01 to 0.2:1.

The ratio of water to silicon in the acid-treated precursor in the third step may preferably be, in terms of the molar ratio, water:silicon=5 to 200:1, more preferably water:silicon=15 to 50:1.

The ratio of the template compound to silicon in the acid-treated precursor in the third step may preferably be, in terms of the molar ratio, template compound:silicon=0.1 to 5:1, more preferably template compound:silicon=0.3 to 3:1, still more preferably template compound:silicon=0.5 to 2.

As for the conditions of hydrothermal synthesis in the third step, the same conditions as described for the first step may be applied. However, when a compound containing titanium is co-present in the third step, it is possible that the adequate synthesis condition is considerably different from that in the first step. Particularly, with respect to the temperature and time, it is desirable to select the condition depending on the element-containing compound to be co-present, so as to provide an intended precursor (B) having a high purity.

In addition, as an embodiment of the third step, it is also possible to use a so-called dry gel method wherein a mixture (mixture X) of the acid-treated precursor and the element-containing compound provided in the second step, and a mixture of water and the template compound (mixture Y) are charged separately, and the mixture (mixture X) of the acid-treated precursor provided in the second step and the metal-containing compound is caused to contact the vapor of water and the template compound. In this case, there is a merit that the template compound which has not been used for the crystallization can be recovered easily.

The mixture X can be obtained by a method wherein a solution of an element-containing compound is dispersed in the acid-treated precursor obtained in the second step as uniformly as possible by use of impregnation, dipping, etc., then dried, and pulverized as desired. It is preferred to use a titanium-containing compound which can be formed into a homogeneous solution. For example, it is preferred to use a compound such as titanium peroxide which can be obtained by reacting an alkoxy titanium and aqueous hydrogen peroxide. The drying can be conducted by various methods such as air drying at room temperature, vacuum drying at high temperature. In general, an aqueous solution is frequently used, and therefore it is sufficient to effect the drying at 50-80° C. for 1-24 hours. The end point of the drying is such that the product in a crushable state.

The mixture Y may be obtained by mixing a template compound and water.

In the dry gel method, the kind of the template compound to be used, the kind of the element-containing compound to be co-present, the ratio of the element being co-present to silicon in the precursor, and the ratio of the template compound to silicon in the precursor may be the same as those as described in the case of the above-described normal hydrothermal synthesis.

The ratio of water to silicon in the precursor is different from the normal hydrothermal synthesis in the adequate range, and may preferably be in terms of molar ratio, water:silicon=0.01-15:1, more preferably is water:silicon=0.1-10:1.

The method of charging the mixture X and the mixture Y may be any method, as long as the mixture X and the mixture Y cannot be mixed with each other unless the mixture Y is heated to be vaporized. For example, it is possible to achieve such charging by a method wherein the mixture Y is placed in the bottom of an autoclave and a container containing the mixture X is hung in the middle part of the autoclave.

As for the conditions of hydrothermal synthesis in the third step, the same conditions as described for the first step may be applied.

Further, it is also possible to obtain a modified layered substance rather than a zeolite substance having a three-dimensional ordered structure, by modifying the state of the superposition of layers by conducting the following between the third step or third-2 step and the fourth step.

Third-3 Step a step of heating the precursor (B) obtained in the third step or acid treated precursor obtained in the third-2 step in the presence of a swelling agent so as to swell the layered precursor, to thereby modify the state of the superposition of layers.

Hereinbelow, the precursors (B) obtained in any of the third step, third-2 step and third-3 step are inclusively referred to as "precursor (B)", in some casses.

The "swelling agent" to be used in the third-3 step is an agent having an action of penetrating into a position between layers of a layered precursor for an MWW-type zeolite substance, by intercalation, etc., and as a result, enlarging the distance between the layers to thereby swell the precursor. The swelling agent is not particularly limited, as long as it can be removed by calcination. In general, it is possible to use a surfactant, preferably a quaternary ammonium salt or amine having at least one long alkyl group. Particularly preferred examples thereof may include trimethyl ammonium salt and triethyl ammonium salt having one alkyl chain of 8-20 carbon atoms, dimethyl ammonium salt or diethyl ammonium salt having two of such an alkyl chain. Further, it is also possible to use a primary or secondary amine compound having at least one alkyl chain of 8-20 carbon atoms, or mixtures thereof. In the case of quaternary ammonium salt, it may be any of chloride, bromide, hydroxide, and iodide. In the case of halide, it is preferred to use a product obtained by hydrolyzing at least a part of the halide to be converted into hydroxide, in the co-presence of aqueous ammonia or another quaternary ammonium salt such as tetramethyl ammonium hydroxide, tetraethyl ammonium hydroxide, and tetrapropyl ammonium hydroxide. Particularly preferred examples of the swelling agent may include lauryl trimethyl ammonium chloride, bromide, hydroxide, cetyl trimethyl ammonium chloride, bromide, hydroxide, stearyl trimethyl ammonium chloride, bromide, hydroxide, distearyl dimethyl ammonium chloride, bromide, hydroxide, etc.

The temperature in the third-3 step is not particularly limited, but it is preferred to use room temperature to 170° C., more preferably 50-150° C. When the temperature is too high, the precursor can be dissolved in some cases, and therefore it is necessary to search a suitable condition, e.g., by relatively lowering the pH.

A pH range of 10-14 is suitable at the time of the processing in the third-3 step. Herein, the "pH at the time of the processing" refers to the pH value obtained by measuring the resultant mixture at room temperature after mixing the acid-treated precursor, swelling agent, others, water or all of the additives such as quaternary ammonium hydroxide. It is necessary to adjust the amount of the swelling agent, the amount of the precursor to be processed, and the amount of quaternary ammonium hydroxide to be added so as to provide an adequate pH range. If the pH is too low, the swelling becomes insufficient, and if the pH is too high, the crystal structure of the layered precursor can be disturbed, and even dissolved in an extreme case.

The processing time is not particularly limited, but 5 minutes to two days is suitable.

In order to modify the state of superposition of layers, it is possible to achieve the modification to some extent by subjecting the swollen layered precursor as such to the fourth step. However, it is preferred that the swollen layered precursor is agitated further vigorously, or the precursor is irradiated with ultrasonic waves so as to effect layer exfoliation (delamination) of at least a part of the layered precursor, to thereby form a so-called card house type structure.

In this case, for example, it is possible to treat the precursor by using an ultrasonic irradiation machine having an output of 50 W or more, for 10 minutes to 2 hours.

The slurry after the layer exfoliation can be recovered as such by filtration and centrifugal separation, but it is possible that an acid is added to the liquid to lower the pH to about 2 so as to promote the precipitation of solid contents, and then the solid contents are separated from the processed liquid and recovered.

The third-3 step may be conducted after the third-2 step. It is also possible to conduct the third-3 step after the third step, without conducting the third-2 step.

The fourth step is described below. The fourth step is a step of calcining the precursor (B) obtained in any of the third step, third-2 step and third-3 step to obtain the titanosilicate.

The method for the calcination of precursor performed between the first step and the second step (first-2 step) and in the fourth step is not particularly limited and the calcination can be performed under conditions known for normal catalyst calcination. The calcination may be performed in a closed system or a flow system and as long as an oxygen necessary for the burning of the template compound is present. The calcination in the air is most easy, but it is also possible that for the purpose of avoiding the excessive heat production, the precursor is heated to a predetermined temperature in an inert gas stream such as nitrogen to degrade the template inside, and then oxygen is introduced to thereby remove the residue by burning. The calcination temperature may preferably be from 200 to 700° C., more preferably from 300 to 650° C., most preferably from 400 to 600° C. If the calcination temperature is less than 200° C., the template compound may not be satisfactorily removed, whereas if it exceeds 700° C., the MWW-type crystal structure may be broken and this disadvantageously causes an adverse effect on the precursor performance in the case of calcination between the first step and the second step and on the titanosilicate in the case of calcination of the fourth step.

The temperature rising rate at the calcination may preferably be 1° C./min but is not limited thereto if breakage of the MWW-type crystal structure does not occur.

The production process of titanosilicate of the present invention (II) is described in more detail below. The production process of an MWW-type zeolite substance of the present invention (I) is described more specifically below, while referring to FIG. 1 as a view for schematically showing the series of these steps. Referring to FIG. 1, the production process of the present invention (I) is a method wherein a layered precursor (A) to be converted into an MWW-type borosilicate is synthesized from a boric acid and a silicon-containing compound using piperidine or hexamethyleneimine as the template (the above procedure is the first step), and acid-treating the layered precursor borosilicate (the above procedure is the second step) to synthesize a deboronated silicate (acid-treated precursor). Prior to the second step, it is also possible to calcine the layered precursor to be converted into the MWW-type borosilicate (the first-2 step). Then, an titanium-containing layered precursor is synthesized from the deboronated silicate and an titanium-containing compound using piperidine or hexamethyleneimine as the template (the above procedure is the third step), and calcining the titanium-containing layered precursor (the above procedure is the fourth step) to remove the template, whereby a zeolite substance having an MWW structure is obtained. FIG. 1 is a view for schematically showing the series of these steps.

The titanosilicate which can be obtained by the production process of the present invention (II) can be used as it is as a catalyst in an oxidation reaction, however, the anatase phase generated as a result of condensation of titanium itself present in the titanosilicate obtained by the production process and not contributing to the oxidation reaction can be at least partially removed by contacting it with an acid. By this contacting with an acid, a titanosilicate catalyst having higher performance can be obtained.

The contacting with an acid as used herein is effective even if it is performed before or after or both before and after the calcination in the fourth step, but this treatment is most effective when applied in the precursor state before the calcination (third-2 step). In particular, the production of anatase phase as a by-product can be greatly inhibited.

The "contacting with an acid" used here and the "contacting with an acid" described with respect to the second step have the same meaning and as for the contacting method, the acid used for the contacting, the concentration of acid used for the contacting, the timing of contacting and when the acid is used as a solution, the solvent and the like, the conditions described with respect to the second step can be applied.

The present invention (III) is described below. The present invention (III) is a process for producing an oxidized compound, comprising performing an oxidation reaction of an organic compound using an oxidizing agent in the presence of the titanosilicate of the present invention (I).

The oxidizing agent which can be used in the present invention (III) specifically includes, for example, oxygen or peroxides. Examples of the peroxide include hydrogen peroxide and an organic peroxide. Examples of the organic peroxide include tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, ethylnaphthalene hydroperoxide and peracetic acid, however, the present invention is not limited thereto. These peroxides may be used in combination of two or more thereof. In the case of ammoximation, ammonia may be added to the peroxide.

The peroxide is most preferably hydrogen peroxide. An aqueous hydrogen peroxide solution having a concentration of 30 mass %, 60 mass % or 90 mass % can be used. The amount of the peroxide added is not particularly limited and may be equivalent or more to the carbon-carbon double bond or carbon-oxygen double bond contained in the organic compound as the raw substance subjected to the oxidation reaction or depending on the conditions, may be equivalent or less.

The organic compound used in the a process for producing an oxidized compound of the present invention (III) may or may not contain one or more other functional group as long as it is a compound having a carbon-carbon double bond or carbon-oxygen double bond within one molecule. In this case, the "other functional group" of course includes a carbon-carbon double bond or carbon-oxygen double bond.

Specific examples of the other functional group include an alkenyl group, an alkynyl group, an aryl group, an arene group, an alcohol group, a phenol group, an ether group, an epoxide group, a halogen group, an aldehyde group, a ketone group, a carbonyl group, an ester group, an amide group, a cyanate group, an isocyanate group, a thiocyanate group, an amine group, a diazo group, a nitro group, a nitrile group, a nitroso group, a sulfide group, a sulfoxide group, a sulfone group, a thiol group, an orthoester group, a urea group and an imino group, however, the present invention is not limited thereto. The compound may have two or more same functional groups or may have two or more kinds of functional groups.

More specific examples of the organic compound include alkenes having from 2 to 10 carbon atoms, cycloalkenes having from 4 to 10 carbon atoms, allyl ethers, compounds having 3 to 10 carbon atoms, ethers of polyhydric alcohol, cycloalkanones having from 4 to 10 carbon atoms and carboxylic acid esters. Of course, a mixture of two or more thereof may be used.

More specifically, examples of the alkenes having from 2 to 10 carbon atoms include ethylene, propylene, butene, pentene, hexene, heptene, octene, nonene, decene, 2-butene, isobutene, 2-pentene, 3-pentene, 2-hexene, 3-hexene, 4-methyl-1-pentene, 2-heptene, 3-heptene, 2-octene, 3-octene, 2-nonene, 3-nonene, 2-decene and 3-decene. Examples of the cycloalkenes having from 4 to 10 carbon atoms include cyclobutene, cyclopentene, cyclohexene, cycloheptene, cyclooctene, cyclononene and cyclodecene.

Examples of the allyl ethers include allyl methyl ether, allyl ethyl ether, allyl propyl ether, allyl butyl ether, allyl vinyl ether and diallyl ether. Examples of the compounds having from 3 to 10 carbon atoms include allyl alcohol, allyl bromide, allyl chloride, acrolein, methacrolein and acrylic acid.

Examples of the ethers of polyhydric alcohol include ethylene glycol monoalkenyl ether, ethylene glycol dialkenyl ether, 1,2-propanediol monoalkenyl ether, 1,2-propanediol dialkenyl ether, 1,3-propanediol monoalkenyl ether, 1,3-propanediol dialkenyl ether, 1,2-butanediol monoalkenyl ether, 1,2-butanediol dialkenyl ether, 1,3-butanediol monoalkenyl ether, 1,3-butanediol dialkenyl ether, 1,4-butanediol monoalkenyl ether, 1,4-butanediol dialkenyl ether, pentaerythritol monoalkenyl ether, pentaerythritol dialkenyl ether, pentaerythritol trialkenyl ether and pentaerythritol tetraalkenyl ether.

Examples of the cycloalkanones having from 4 to 10 carbon atoms include cyclopentanone, cyclohexanone and cycloheptanone.

Examples of the carboxylic acid esters include allyl formate, allyl acetate, allyl tartrate, allyl propionate and allyl methacrylate.

The combination of the organic compound and the oxidizing agent used in the a process for producing an oxidized compound of the present invention (III) is most preferably a combination such that the organic compound is one or more compound selected from the group consisting of propylene, diallyl ether, allyl alcohol, allyl chloride, allyl acetate, allyl methacrylate, cyclohexene and cyclohexanone and the oxidizing agent is hydrogen peroxide.

The amount of titanosilicate used as the catalyst in the a process for producing an oxidized compound of the present invention (III) is not particularly limited. The preferred range thereof varies depending on the kind of oxidation reaction, the reaction temperature, the reactivity and temperature of substrate, the peroxide concentration, the kind and concentration of solvent, and the reaction form (batch system or continuous system). In the case of use in a slurry system, usually, the amount of titanosilicate is, in terms of the concentration in the reactant mixture, suitably from 0.1 to 20 mass %, preferably from 0.5 to 10 mass %. In a fixed bed flow reaction system, titanosilicate may preferably be used in an apparent catalytic amount larger than this range.

The titanosilicate used as the catalyst is not particularly limited on the form and may be used in the form of powder, fine sphere, pellet or extrusion-molded article or may be supported on a support. In molding the catalyst, a binder may be used. The binder and the support each may preferably be a substantially non-acidic or weakly acidic substance which does not accelerate the decomposition reaction of the peroxide or the intended oxide.

The oxidation reaction in the a process for producing an oxidized compound of the present invention (III) may be performed without using a solvent or in the presence of an appropriate solvent. Examples of the appropriate solvent include alcohols, ketones, nitriles and water. Specific examples of the alcohols include methanol, ethanol, 1-propanol, 2-propanol, 1-butanol, 2-butanol, tert-butanol, amyl alcohol, ethylene glycol, propylene glycol and 1,2-butanediol. Specific examples of the ketones include acetone, methyl ethyl ketone and diethyl ketone. Specific examples of the nitriles include acetonitrile, pripionitrile and benzonitrile. These solvents may be used individually or as a mixture. Among these solvents, preferred are acetone, acetonitrile and water, more preferred is acetonitrile.

The reaction temperature at the oxidation reaction in the a process for producing an oxidized compound of the present invention (III) is not particularly limited and may preferably be from 0 to 150° C., more preferably from 10 to 100° C. If the reaction temperature is less than 0° C., the reaction rate is low and not practical, whereas if it exceeds 150° C., the decomposition reaction of the peroxide seriously occurs and also, the decomposition reaction of the intended product may be disadvantageously accelerated.

The oxidation reaction is generally an exothermic reaction and therefore, the heat of reaction may preferably be removed by an appropriate method so as to control the reaction temperature in a constant range. The reaction pressure is not particularly limited.

The oxidation reaction in the a process for producing an oxidized compound of the present invention (III) may be performed in a batch system, a continuous system or a semi-continuous system using an appropriate reactor or reaction device such as fixed bed, transporting bed, stirring slurry or CSTR reactor and any method may be used. The mixture comprising titanosilicate as the catalyst, an organic compound as the substrate and a peroxide may be mixed all at once or in sequence.

In this reaction, the desired oxidized compound can be separated by a separation purification method in the normal purification step. More specifically, for example, when the reaction is preformed in a batch system, the oxidized compound can be separated and recovered from the reaction mixture using an arbitrary known method such as fractional distillation, extractive distillation and liquid-liquid extraction after the amount of the oxidized compound produced reaches the desired level.

In the case of a slurry-type reactor, the titanosilicate catalyst can be recovered by an appropriate method such as filtration or centrifugation and the recovered catalyst can be reused as the catalyst in the oxidation reaction.

On the other hand, in the case of a fixed bed-type reactor, the titanosilicate catalyst can be easily separated, while being held in the reactor, from the product oxidized compound, solvent, unreacted raw substance organic compound and peroxide.

In the a process for producing an oxidized compound of the present invention (III), the recovered titanosilicate catalyst, unreacted raw substance organic compound and peroxide can be again used after these are purified by an appropriate method or without passing through the purification.

Generally, the recovered titanosilicate catalyst for use in the present invention (III) decreases in the activity on repeated use and does not exhibit the initial activity. In such a case, the recovered catalyst must be regenerated. The regeneration of the recovered catalyst can be performed by a conventionally known method. More specifically, the recovered catalyst can be regenerated to the initial activity, for example, by calcining it in air at a temperature of 100 to 600° C.

EXAMPLES

The present invention is described in greater detail below by referring to Examples, however, these Examples only show the outline of the present invention and the present invention is not limited to these Examples.

[Description of Terms in Examples and Comparative Examples]

Calculation Method of Conversion of Allyl Alcohol:

The conversion of allyl alcohol is shown by a molar ratio of allyl alcohol consumed in the reaction to the allyl alcohol charged before the reaction. The allyl alcohol consumed in the reaction was calculated from the increase or decrease of allyl alcohol between before and after the reaction. At this time, the allyl alcohol was determined quantitatively by using the GC (gas chromatography) method as described hereinafter.

Calculation Method of Selectivity of Glycidol:

The selectivity of glycidol is shown by a molar ratio of glycidol and glycerin calculated from the analysis results of the filtrate after the reaction. At this time, the glycidol and glycerin were determined quantitatively by using the GC method as described hereinafter.

Calculation Method of Conversion of Hydrogen Peroxide:

The conversion of hydrogen peroxide is shown by a ratio of hydrogen peroxide consumed in the reaction to the hydrogen peroxide charged before reaction. The hydrogen peroxide consumed in the reaction was calculated from the increase or decrease of hydrogen peroxide between before and after the reaction. At this time, the hydrogen peroxide was determined quantitatively by using the titration method as described hereinafter.

Calculation of Efficiency of Hydrogen Peroxide:

The efficiency of hydrogen peroxide is shown by a ratio of hydrogen peroxide consumed in the reaction excluding the hydrogen peroxide consumed in the decomposition into oxygen, namely, a ratio of hydrogen peroxide consumed in the epoxidation reaction out of the hydrogen peroxide consumed.

Yield of Epoxide:

This yield is an yield of epoxide compound as an intended oxidized compound, based on hydrogen peroxide, after the completion of oxidation reaction using hydrogen peroxide and shown by a molar ratio of the amount of the epoxy compound produced to the hydrogen peroxide charged.

[Analyzers in Examples and Comparative Examples]

Analysis Method of Titanosilicate Element

Titanosilicate was weighed into a Teflon (registered trademark of E.I. du Pont de Nemours and Company) beaker and hydrofluoric acid (50 mass %) was added and dissolved. Pure water was added thereto and the component analysis was performed using a desk-type inductively coupled plasma spectrometer (JY38S) manufactured by Rigaku.

Measuring Method of Infrared Absorption Spectrum of Titanosilicate 100 mg of a solid of potassium bromide containing 3 mass % of a sample titanosilicate was pelletized, set in a quartz-made cell and degassed at 500° C. for 1 hour under a pressure of $10^{-3}$ Pa. This sample was cooled to room temperature and measured on the spectrum using an infrared spectrometer (FTIR-8100) manufactured by Shimadzu Corporation. The FT-IR conditions used in this case were as follows.

<FT-IR Conditions>
Measuring range: 400-4000 $cm^{-1}$
Resolution: 2 $cm^{-1}$
Integration times: 16 times-128 times Ultraviolet Visible Absorption Spectrum Method (U V)

The ultraviolet visible absorption spectrum of a sample was measured by a diffuse reflection method by use of the following apparatus, and conditions.

Apparatus: JASCO UV/VIS spectrometer V-550 mfd. by Nihon Bunko Company
Measurement range: 200-500 nm
Standard material for base line: $BaSO_4$ Powder X-ray Diffraction Method (XRD)

The powder X-ray diffraction pattern of a sample was measured by using the following apparatus and conditions.

Apparatus: MX-Labo powder X-rays analysis apparatus mfd. by Mac Science Company
Radiation source: CuKα ray (1.5405 Angstrom)
Condition: Output 40 kV-20 mA
Range: 2Θ=5-50°
Scanning rate: 2°/minute Analysis of Organic Compound Concentration in Filtrate of Reaction Mixture:

The concentration was measured by the following gas chromatography analyzer under the following conditions.

The analysis was performed according to an internal standard method by injecting a 0.4 μl portion of the analysis solution which was obtained by adding 1 ml of 1,4-dioxane as the internal standard to 10 ml of the reaction solution.

Gas Chromatography:

GC-14B manufactured by Shimadzu Corporation Column:
capillary column TC-WAX (length: 30 m, inner diameter: 0.25 mm, membrane thickness: 0.25 μm) Carrier gas:
nitrogen (split ratio: 20, column flow rate: 2 ml/min)

Temperature Conditions:

The detector and the vaporization chamber were at a temperature of 200° C., and the column temperature was kept at 50° C. for 5 minutes from the start of analysis, then elevated to 150° C. at a temperature rising rate of 10° C./min, kept at 150° C. for 10 minutes, thereafter elevated to 200° C. at a temperature rising rate of 10° C./min, and kept for 25 minutes.

Detector:

FID ($H_2$ pressure: 70 kPa, air pressure: 100 kPa)

Analysis of Concentration of Hydrogen Peroxide in Filtrate of Reaction Mixture:

A potentiometric titration was performed using an auto-potentiometric titrator AT-012 manufactured by Kyoto Denshi Kagaku Kogyo and using a Ce(IV)-containing solution as the titration reagent.

Example 1

Production of Catalyst 1

[Preparation of Borosilicate and Acid Treatment]

In 684 g of ion exchanged water, 243.2 g of piperidine (produced by Wako Pure Chemical Industries, Ltd., purity: 98%) (hereinafter simply referred to as "PI") was dissolved at 25° C. to prepare an aqueous PI solution. To this aqueous PI solution, 165.8 g of boric acid (produced by Wako Pure Chemical Industries, Ltd., 99.5%) was added while vigorously stirring. After stirring for 30 minutes to completely dissolve the boric acid, 120 g of fumed silica (Cab-o-sil M7D) was added and the stirring was further continued for 2 hours to obtain a mixture of $1.SiO_2:0.67.B_2O_3:1.4.PI:19.H_2O$ (by mol).

This mixture was transferred to a 2 liter-volume Teflon (registered trademark of E.I. du Pont de Nemours and Company)-made autoclave and stirred for 120 hours at a rotation speed of 100 rpm at a temperature of 170° C. After stopping the rotation, the contents were cooled to 25° C. and the solid product was separated from the contents by filtration and washed with ion exchanged water. The washing was repeated until the pH of the washing water became 9 or less.

The obtained solid product was dried at a temperature of 80° C. and calcined at a temperature of 600° C. The resulting solid product was subjected to an acid treatment for 20 hours at a temperature of 100° C. by adding 30 ml of 6 mol/liter nitric acid per g of the solid product. After the completion of acid treatment, the product was filtered and the obtained solid was calcined for 10 hours at a temperature of 600° C. The boron/silicon molar ratio of this solid (Deborosilicate A) was 0.0217. This solid was further subjected to an acid treatment at a temperature of 100° C. for 20 hours by adding 30 ml of 6 mol/liter nitric acid per g of the solid. The solid (Deborosilicate B) obtained by filtration after the completion of acid treatment had a boron/silicon molar ratio of 0.0017.

[Preparation of MWW-Type Titanosilicate]

In 30 g of ion exchanged water, 14.5 g of PI (produced by Wako Pure Chemical Industries, Ltd., purity: 98%) was dissolved at 25° C. to prepare an aqueous PI solution. To this aqueous PI solution, 2.0 g of tetrabutyl orthotitanate (produced by Wako Pure Chemical Industries, Ltd., purity: 95%) was added while vigorously stirring. After stirring for 30 minutes to completely hydrolyze the tetrabutyl orthotitanate, 10 g of the previously prepared Deborosilicate B having a boron/silicon molar ratio of 0.0017 was added and the stirring was further continued for 2 hours to obtain a mixture of $1.SiO_2:0.033.TiO_2:1-PI:10.H_2O$ (by mol).

Figure 2:
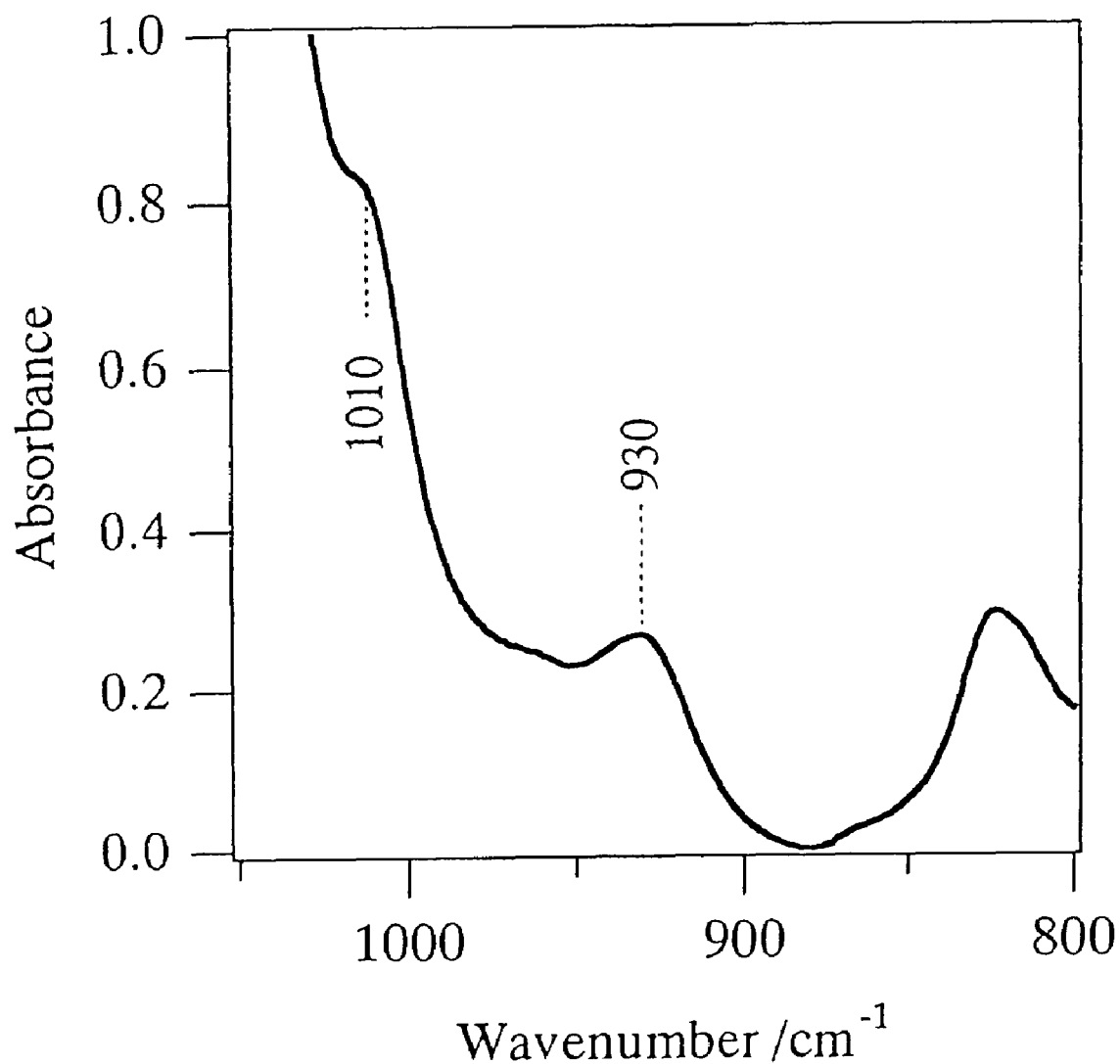
FIG. 2 is an infrared absorption spectrum of titanosilicate produced in Example 1.
Figure 3:
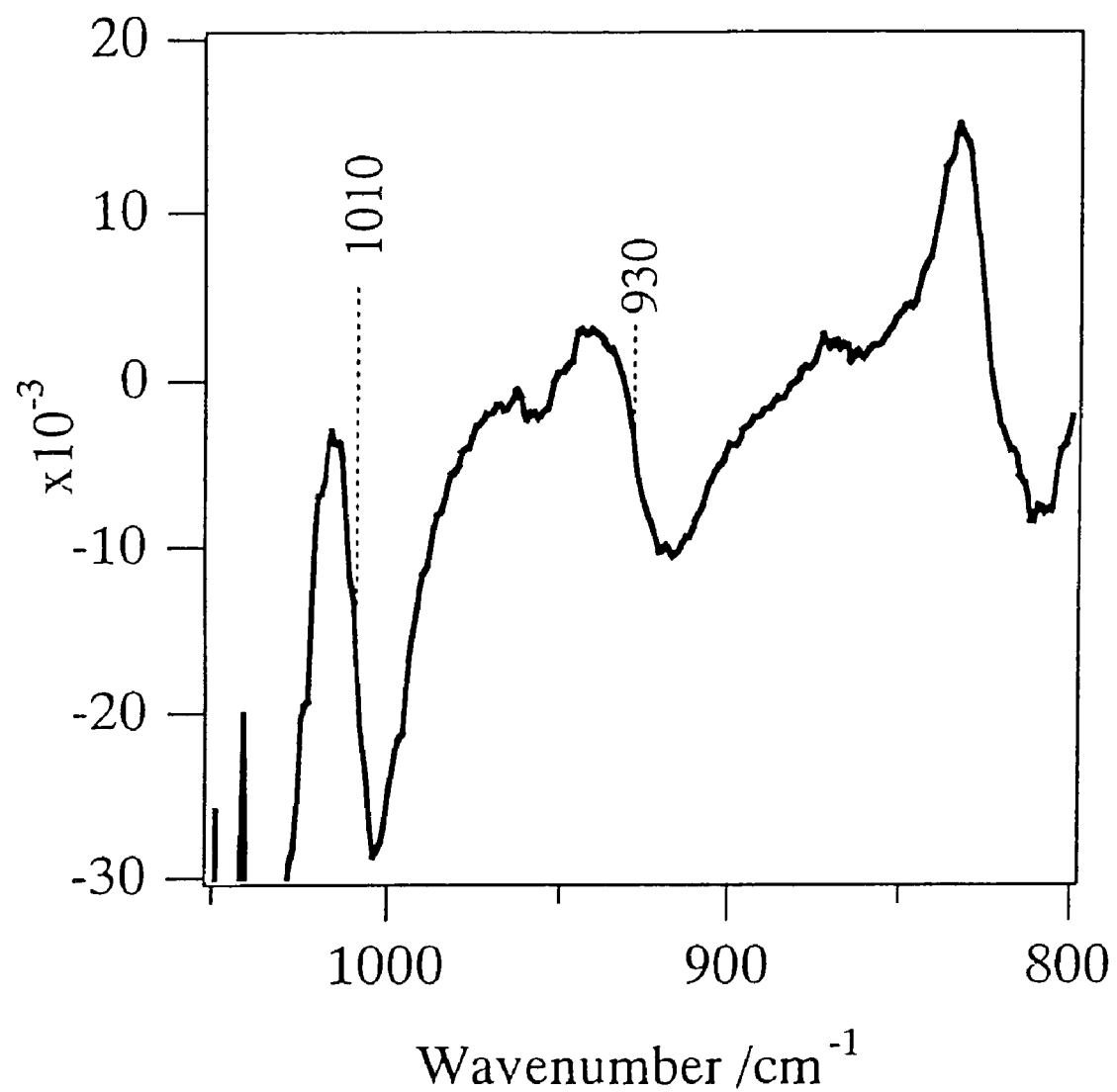
FIG. 3 is the first differential (differential of first order) spectrum of FIG. 2.
Figure 4:
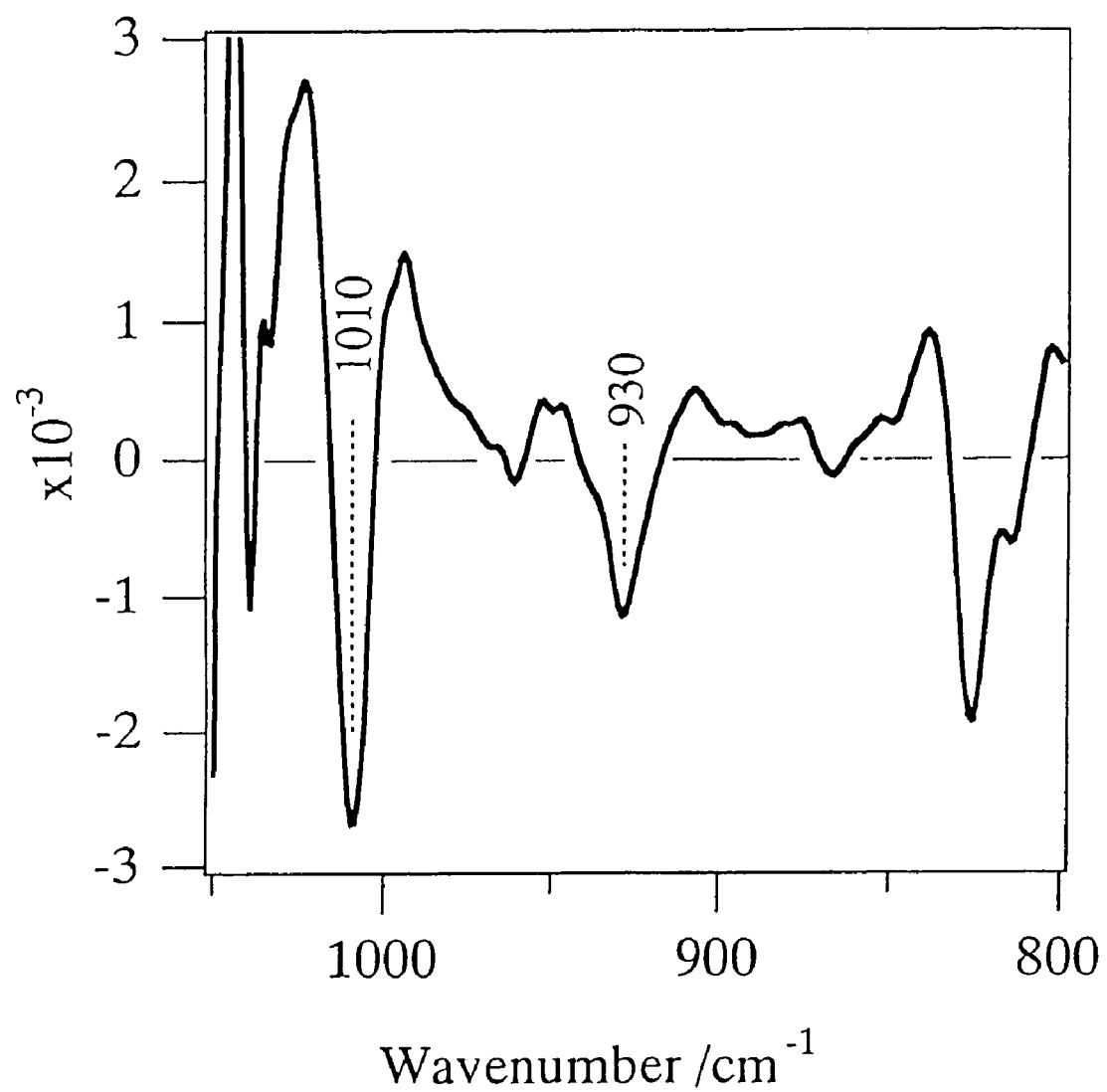
FIG. 4 is the second differential spectrum of FIG. 2.
Figure 5:
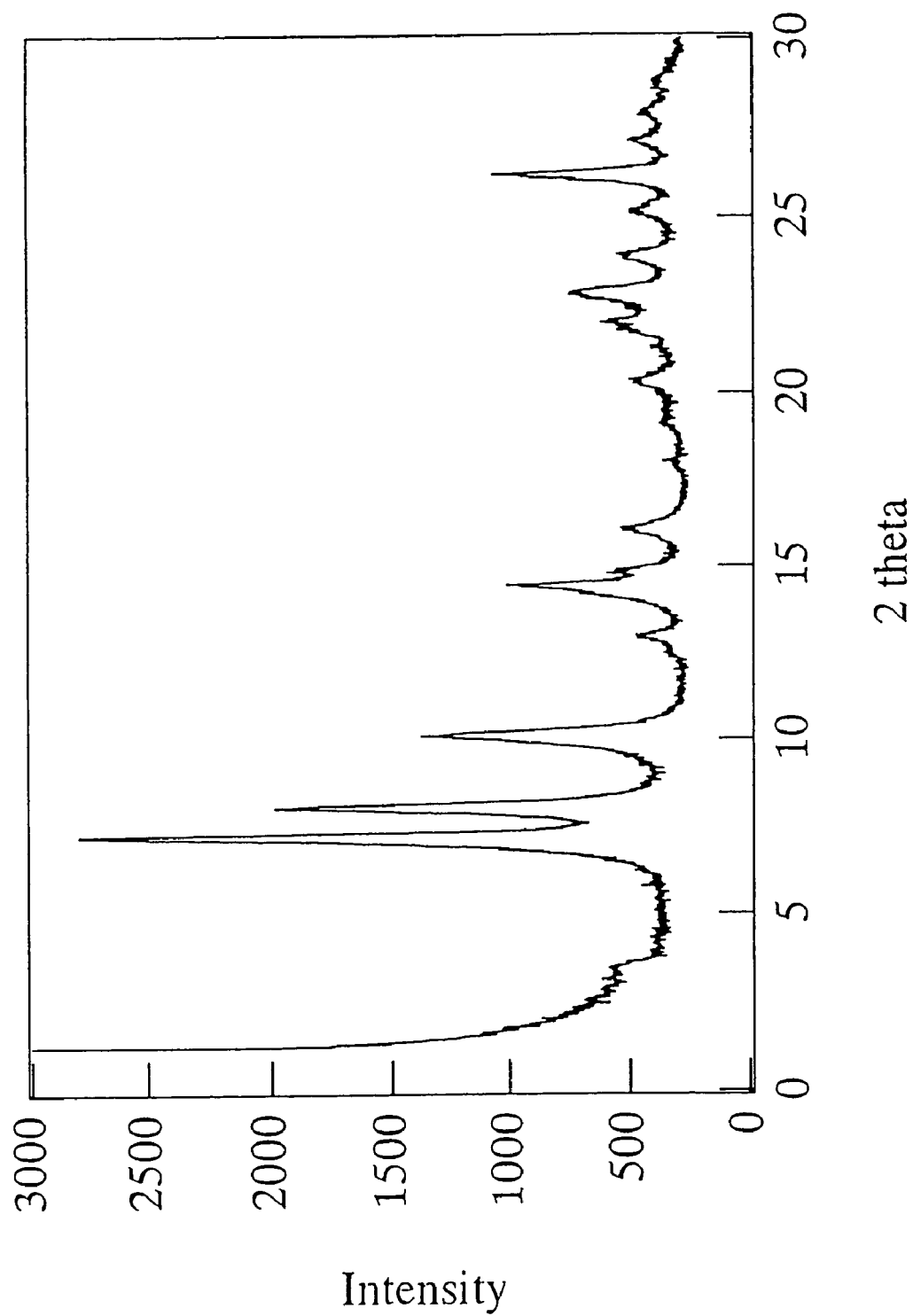
FIG. 5 is an XRD pattern of the-substance obtained in Example 1.
Figure 6:
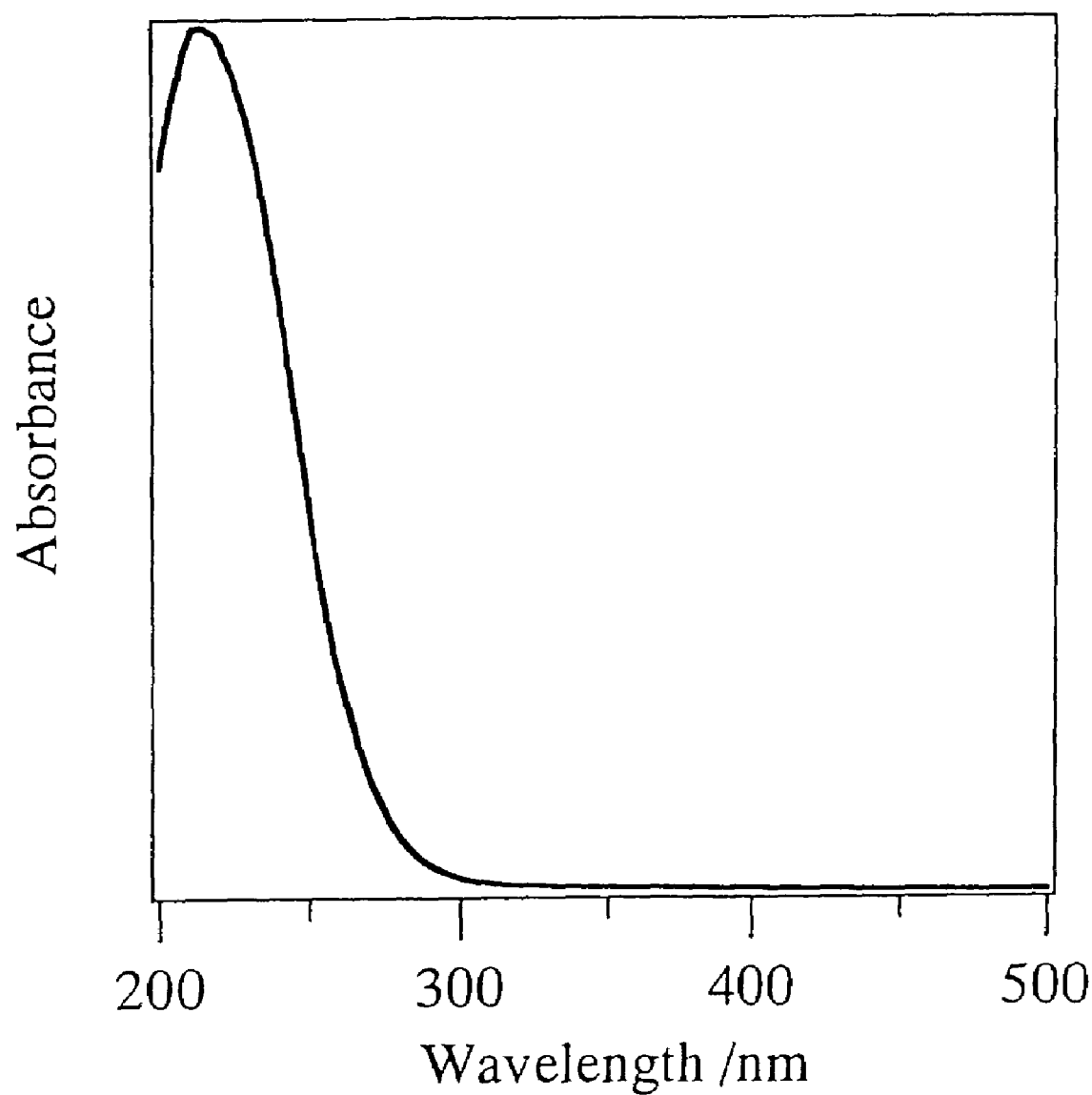
FIG. 6 is a UV spectrum of the substance obtained in Example 1.

This mixture was transferred to a 150 ml-volume Teflon (registered trademark of E.I. du Pont de Nemours and Company)-made autoclave and stirred for 158 hours at a rotation speed of 40 rpm at a temperature of 175° C. After stopping the rotation, the contents were cooled to 25° C. and the solid product was separated from the contents by filtration and washed with ion exchanged water. The washing was repeated until the pH of the washing water became 9 or less. The obtained solid product was dried at a temperature of 80° C. and subjected to an acid treatment for 20 hours at a temperature of 100° C. by adding 20 ml of 2 mol/liter nitric acid per g of the solid product. After the completion of acid treatment, the product was filtered and the obtained solid was calcined for 10 hours at a temperature of 600° C. to obtain an MWW-type titanosilicate catalyst as the final intended product. The titanium/silicon molar ratio of this titanosilicate catalyst was 0.0233 and the boron/silicon molar ratio was 0.0018. Also, the infrared absorption spectrum was measured in the dehydrated state and on the absorption spectrum, an absorption band having a relative maximum value at 930 $cm^{-1}$ was observed. FIG. 2 shows the spectrum. In addition, FIGS. 3 and 4 are respectively the first differential spectrum of this absorbance spectrum, and the second differential spectrum of this absorbance spectrum. In the second differential spectrum, the curve crosses the zero point of the ordinate axis at about 1010 $cm^{-1}$, and has a relative minimum value in the neighborhood of 1010 $cm^{-1}$. Accordingly, it was found that there is an absorption band having a relative maximum value in the neighborhood of 1010 $cm^{-1}$ is present. Further, an XRD pattern and an UV-VIS spectrum of this sample are respectively shown in FIGS. 5 and 6.

Example 2

Production of Catalyst 2

[Preparation of MWW-Type Titanosilicate]

In an aqueous solution containing 2 g of ion exchanged water and 1 g of hydrogen peroxide (produced by Wako Pure Chemical Industries, Ltd., purity: 31%), 0.2 g of tetrabutyl orthotitanate (produced by Wako Pure Chemical Industries, Ltd., purity: 95%) was added at 25° C. The tetrabutyl orthotitanate was completely hydrolyzed by the stirring for 30 minutes and then dissolved by the stirring for 30 minutes. Thereto, 9 g of ion exchanged water and 10 g of Deborosilicate A having a boron/silicon molar ratio of 0.0217 prepared in Example 1 were added and the stirring was further continued for 10 minutes. Thereafter, the water content was evaporated over 3 hours at a temperature of 100° C. while stirring to obtain a mixture of $1.SiO_2$: $0.033.TiO_2$ (by mol).

This solid mixture was placed in a 5 ml-volume Teflon (registered trademark of E.I. du Pont de Nemours and Company)-made beaker and the beaker was transferred to a 50 ml-volume Teflon (registered trademark of E.I. du Pont de Nemours and Company)-made autoclave previously containing 1.5 g of ion exchanged water and 2.5 g of PI (produced by Wako Pure Chemical Industries, Ltd., purity: 98%) and statically heated at a temperature of 170° C. for 158 hours. After the completion of heating, the contents were cooled to 25° C. and the solid product was separated from the contents by filtration and washed with ion exchanged water. The washing was repeated until the pH of the washing water became 9 or less. The obtained solid product was dried at a temperature of 80° C. and subjected to an acid treatment for 20 hours at a temperature of 100° C. by adding 100 ml of 2 mol/liter nitric acid per g of the solid product. After the completion of acid treatment, the product was filtered and the obtained solid was calcined for 10 hours at a temperature of 600° C. to obtain an MWW-type titanosilicate catalyst as the final intended product. The titanium/silicon molar ratio of this titanosilicate catalyst was 0.0167 and the boron/silicon molar ratio was 0.0018. Also, the infrared absorption spectrum was measured in the dehydrated state and on the spectrum, an absorption band having a relative maximum value at 930 $cm^{-1}$ was observed.

The titanium/silicon molar ratio and boron/silicon molar ratio of Catalysts 1 and 2 obtained in Examples 1 and 2 are shown in Table 3.

[Table 3]

TABLE 3

| No. | | Titanium/Silicon Molar Ratio | Boron/Silicon Molar Ratio |
|---|---|---|---|
| Example 1 | Catalyst 1 | 0.0233 | 0.0018 |
| Example 2 | Catalyst 2 | 0.0167 | 0.0018 |

Example 3

Production of Oxidized Compound Using Titanosilicate Catalyst 1

In a 20 ml-volume three-neck flask equipped with a thermometer, a reflux condenser and a magnetic stirrer, 0.58 g (10 mmol) of allyl alcohol and 3.9 g (5 ml) of acetonitrile were added and then the MWW-Type titanosilicate catalyst (50 mg) prepared in Example 1 was charged. The mixture was heated in a hot bath at 60° C. and vigorously stirred. Immediately after the temperature of the reaction mixture reached 57° C., 1.1 g (10 mmol as hydrogen peroxide) of an aqueous 30 mass % hydrogen peroxide solution were added to the system. By setting the reaction start time to this point, the stirring was continued until the passing of 30 minutes from the start of reaction. After 30 minutes from the start of reaction, the reaction mixture was immediately cooled with ice bath to stop the reaction. Thereafter, the reaction mixture was filtered to separate unreacted allyl alcohol, unreacted hydrogen peroxide, water, product and solvent from the catalyst. At this time, the concentration of organic substance in the obtained filtrate was analyzed by gas chromatography and the concentration of unreacted hydrogen peroxide was determined by potentiometric titration using Ce(IV). The reaction results are shown in Table 4. The conversion of allyl alcohol was 95.9%, the selectivity of glycidol as the produced epoxy compound was 99.7%, the conversion of hydrogen peroxide was 97.6% and the efficiency of hydrogen peroxide was 98.0%.

TABLE 4

| | Kind of Catalyst | | | |
|---|---|---|---|---|
| No. | | Titanium/Silicon Molar Ratio* | Boron/Silicon Molar Ratio*5 | Solvent Used in Reaction |
| Example 3 | Catalyst 1 | 0.0233 | 0.0018 | acetonitrile |
| Example 4 | Catalyst 2 | 0.0167 | 0.0018 | acetonitrile |
| Comparative Example 1 | [Ti, B]-MWW type | 0.0217 | 0.0204 | acetonitrile |
| Comparative Example 2 | MFI type | 0.0192 | — | acetonitrile |

| | Conversion (%) | | Selectivity (mol %)*3 | | Efficiency of Hydrogen Peroxide*4 (%) |
|---|---|---|---|---|---|
| | Allyl Alcohol*1 | Hydrogen Peroxide*2 | Glycidol | Glycerin | |
| Example 3 | 95.9 | 97.6 | 99.7 | 0.3 | 98.0 |
| Example 4 | 97.0 | 98.0 | 100 | 0 | 99.0 |
| Comparative Example 1 | 77.1 | 79.5 | 99.0 | 1.0 | 96.0 |
| Comparative Example 2 | 20.6 | 19.3 | 88.0 | 12.0 | 94.0 |

*1 Conversion of allyl alcohol: Allyl alcohol consumed (mol)/raw substance allyl alcohol (mol) × 100 (%)
*2 Conversion of hydrogen peroxide: Hydrogen peroxide consumed (mol)/raw substance hydrogen peroxide (mol) × 100 (%)
*3 Selectivity of glycidol: Glycidol (mol)/{glycidol (mol) + glycerin (mol)} × 100 (mol %) Selectivity of glycerin: Glycerin (mol)/{glycidol (mol) + glycerin (mol)} × 100 (mol %)
*4 Efficiency of hydrogen peroxide: {Glycidol (mol) + glycerin (mol)}/hydrogen peroxide consumed (mol) × 100 (%)
*5 Molar ratio (calculated by ICP emission spectroscopic analysis)

Example 4

Production of Oxidized Compound Using Titanosilicate Catalyst 2

The same operation as in Example 3 was performed except for using the MWW-type titanosilicate catalyst (50 mg) prepared in Example 2. The reaction results are shown in Table 4. The conversion of allyl alcohol was 97.0%, the selectivity of glycidol as the produced epoxy compound was 100%, the conversion of hydrogen peroxide was 98.0% and the efficiency of hydrogen peroxide was 99.0%.

Comparative Example 1

Comparative Catalyst-1; Production of MWW-Type Titanosilicate by Direct Synthesis Method and Production of Oxidized Compound In 513 g of ion exchanged water, 182.5 g of PI (produced by Wako Pure Chemical Industries, Ltd., purity: 98%) was dissolved at 25° C. to prepare an aqueous PI solution. This aqueous PI solution was equally divided into two portions and while vigorously stirring, 18.0 g of tetrabutyl orthotitanate (produced by Wako Pure Chemical Industries, Ltd., purity: 95%) was added to one portion and 124.2 g of boric acid (produced by Wako Pure Chemical Industries, Ltd., 99.5%) was added to another portion. After stirring for 30 minutes to completely hydrolyze the tetrabutyl orthotitanate, 45 g of fumed silica (Cab-o-sil M7D) was added to each solution containing titanium or boron. After the addition of silica, these solutions were stirred for 1 hour to obtain two kinds of uniform gels. These two kinds of gels were mixed and the stirring was further continued for 1 hour and 30 minutes to obtain a mixture of $1.SiO_2:0.033.TiO_2:0.67.B_2O_3:1.4.PI:19.H_2O$ (by mol).

Figure 7:
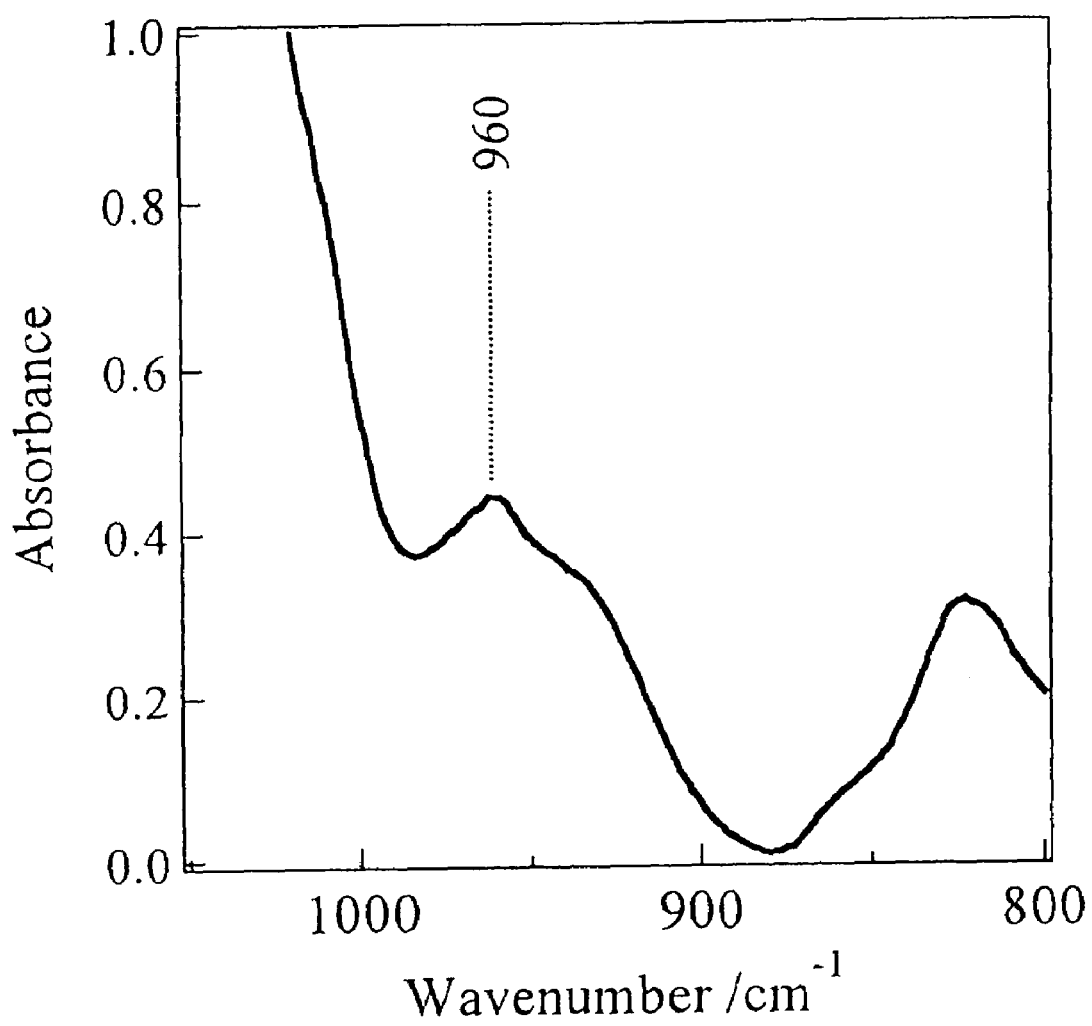
FIG. 7 is an infrared absorption spectrum of the substance obtained in Comparative Example 1.

This gel was transferred to a 2 liter-volume Teflon (registered trademark of E.I. du Pont de Nemours and Company)-made autoclave, stirred for 24 hours at a rotation speed of 100 rpm at a temperature of 130° C., then stirred for 24 hours at a rotation speed of 100 rpm at a temperature of 150° C. and further stirred for 120 hours at a rotation speed of 100 rpm at a temperature of 170° C. After stopping the rotation, the contents were cooled to 25° C. and the solid product was separated from the contents by filtration and washed with ion exchanged water. The washing was repeated until the pH of the washing water became 9 or less. The obtained solid product was dried at a temperature of 50° C. and subjected to an acid treatment for 20 hours at a temperature of 100° C. by adding 20 ml of 6 mol/liter nitric acid per g of the solid product. After the completion of acid treatment, the product was filtered and the obtained solid was calcined for 10 hours at a temperature of 530° C. to obtain an MWW-type titanosilicate catalyst. The titanium/silicon molar ratio of this titanosilicate catalyst was 0.0217 and the boron/silicon molar ratio was 0.0204. Also, the infrared absorption spectrum was measured in the dehydrated state and on the spectrum, an absorption band having a relative maximum value at 960 cm$^{-1}$ was observed. FIG. 7 shows the spectrum.

The same operation as in Example 3 was performed except for using this MWW-type titanosilicate catalyst obtained by the direct synthesis method. The reaction results are shown in Table 4.

Comparative Example 2

Figure 8:
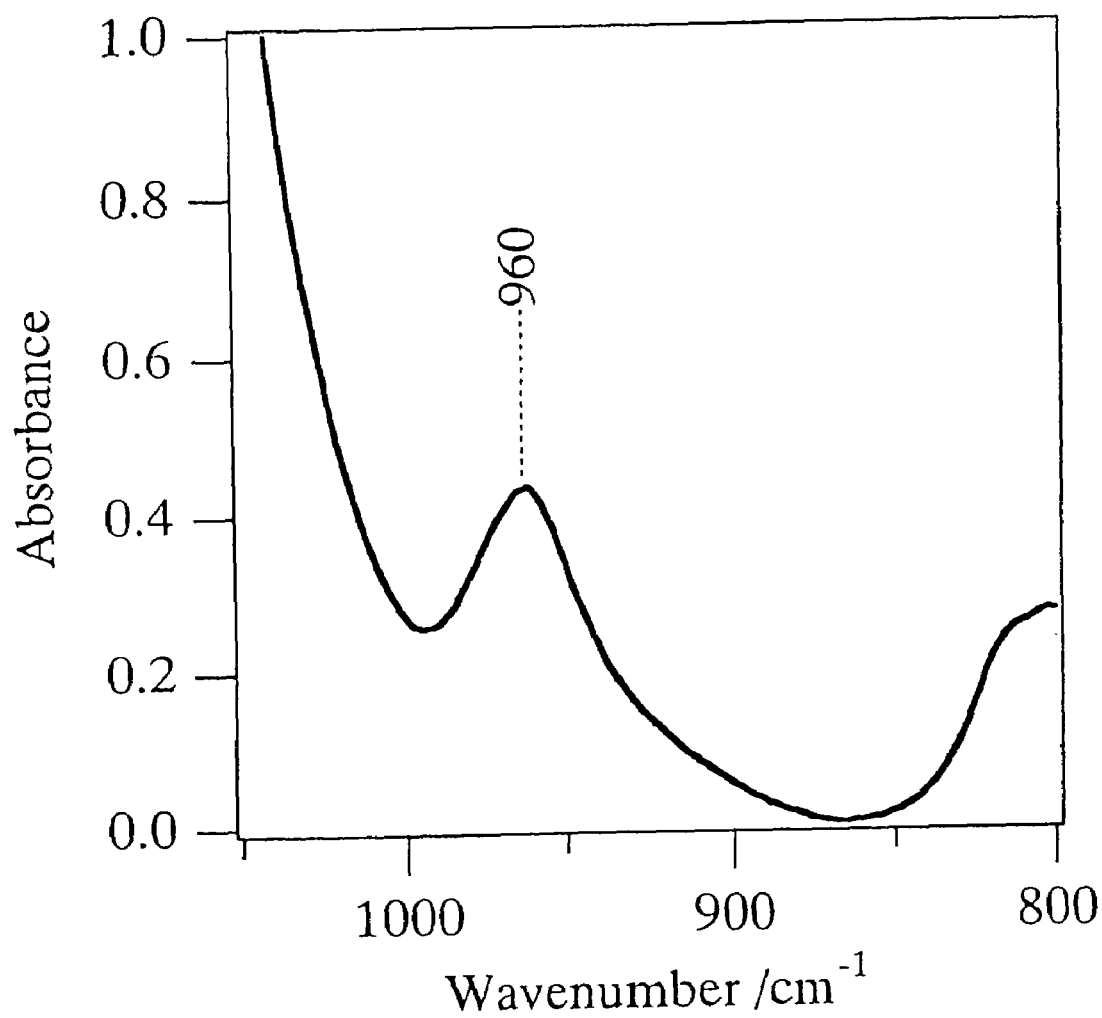
FIG. 8 is an infrared absorption spectrum of the substance obtained in Comparative Example 2.

Comparative Catalyst 2; Production of MFI-Type Titanosilicate Catalyst and Production of Oxidized Compound In a 500 ml-volume beaker equipped with a magnetic stirrer, 62.5 g of tetraethyl orthosilicate (produced by Wako Pure Chemical Industries, Ltd.) was added and then 107 g of an aqueous 20 mass % tetrapropylammonium hydroxide solution (produced by Tokyo Kasei Kogyo) was added at a temperature of 30° C. over 10 minutes. After stirring for 1.0 hour, a mixture containing 38 g of isopropyl alcohol (produced by Wako Pure Chemical Industries, Ltd.) and 14 g of tetrabutyl orthotitanate (produced by Tokyo Kasei) was added over 30 minutes. After stirring at 30° C. for 30 minutes, the mixture was heated using a hot bath at 80° C. and the stirring was continued for 2 hours. To the thus-obtained mixture, 230 g of water was added. The resulting solution was transferred to a Teflon (registered trademark of E.I. du Pont de Nemours and Company)-made autoclave and a hydrothermal synthesis was performed at 175° C. for 48 hours. After the completion of hydrothermal synthesis, the contents were taken out from the autoclave and the solid product was separated by centrifugation. The obtained solid product was washed with distilled water and after the completion of washing, calcined at 500° C. for 8 hours in the presence of air to remove organic substances. The solid matter obtained by the calcination was subjected to acid washing for 12 hours using 20 ml of an aqueous 1.0 mol/liter nitric acid solution per g of the solid matter. After the completion of acid washing, the solid product was separated by filtration and then calcined at 500° C. for 12 hours in the presence of air to obtain the intended MFI-type titanosilicate catalyst having a titanium/silicon molar ratio of 0.0192. Also, the infrared absorption spectrum was measured in the dehydrated state and on the spectrum, an absorption band having a relative maximum value at 960 cm$^{-1}$ was observed. FIG. 8 shows the spectrum.

The same operation as in Example 3 was performed except for using this MFI-type titanosilicate catalyst. The reaction results are shown in Table 4.

Example 5

Study of Reaction Substrate

In a 20 ml-volume three-neck flask equipped with a thermometer, a reflux condenser and a magnetic stirrer, 0.84 g (10 mmol) of 2-hexane and 7.8 g (10 ml) of acetonitrile were added and then the MWW-type titanosilicate catalyst 1 (50 mg) prepared in Example 1 was charged. The mixture was heated in a hot bath at 60° C. and vigorously stirred. Immediately after the temperature of the reaction mixture reached 57° C., 1.1 g (10 mmol as hydrogen peroxide) of 30 mass % hydrogen peroxide was added to the system. By setting the reaction start time to this point, the stirring was continued until the passing of 2 hours from the start of reaction. After 2 hours from the start of reaction, the reaction mixture was immediately cooled with ice to stop the reaction. Thereafter, the reaction mixture was filtered to separate unreacted 2-hexene, unreacted hydrogen peroxide, water, product and solvent from the catalyst. At this time, the concentration of organic substance in the obtained filtrate was analyzed by gas chromatography and the concentration of unreacted hydrogen peroxide was determined by potentiometric titration using Ce(IV). The reaction results are shown in Table 5. The yield of 2,3-epoxyhexane as the intended epoxide compound was 70.0%.

TABLE 5

| | Substrate | Epoxide Product | Yield of Epoxide (%)*1 |
|---|---|---|---|
| Example 5 | 2-hexene | 2,3-epoxyhexane | 70.0 |
| Example 6 | cyclohexene | cyclohexene oxide | 7.5 |
| Comparative Example 3 | 2-hexene | 2,3-epoxyhexane | 50.3 |
| Comparative Example 4 | cyclohexene | cyclohexene oxide | 2.2 |
| Comparative Example 5 | 2-hexene | 2,3-epoxyhexane | 16.8 |
| Comparative Example 6 | cyclohexene | cyclohexene oxide | 0.9 |

*1Yield of epoxide:

Amount of epoxide produced (mol)/amount of raw substance hydrogen peroxide (mol)×100 (%)

Example 6

The same operation as in Example 5 was performed except for using 0.82 g (10 mmol) of cyclohexene and 0.55 g (5 mmol as hydrogen peroxide) of 30 mass % hydrogen peroxide. The reaction results are shown in Table 5. The yield of cyclohexene oxide as the intended epoxide compound was 7.5%.

Comparative Examples 3 and 4

The same operations as in Examples 5 and 6 were performed except for using the MWW-type titanosilicate catalyst obtained by direct synthesis method in Comparative Example 1. The reaction results are shown in Table 5. The yield of 2,3-epoxyhexane as the intended epoxide compound was 50.3% and the yield of cyclohexene oxide was 2.2%.

Comparative Examples 5 and 6

The same operations as in Examples 5 and 6 were performed except for using the MFI-type titanosilicate catalyst obtained in Comparative Example 2. The reaction results are shown in Table 4. The yield of 2,3-epoxyhexane as the intended epoxide compound was 16.8% and the yield of cyclohexene oxide was 0.9%.

Example 7

Preparation of MWW Type Titanosilicate of Various Si/Ti Ratios

Figure 9:
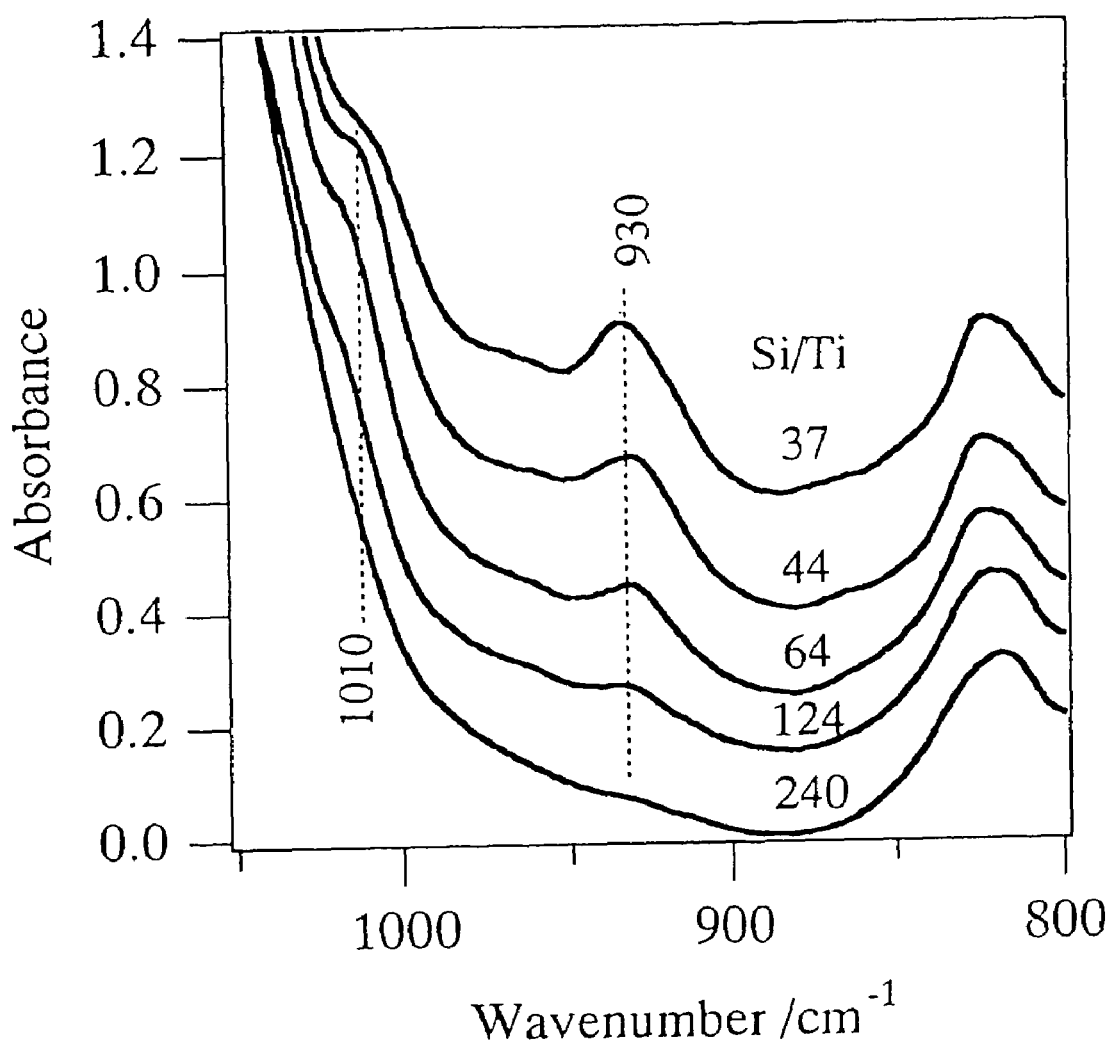
FIG. 9 is infrared absorption spectra of MWW type titanosilicate substances having various Si/Ti ratios obtained in Example 7.

Five kinds of MWW-type titanosilicate substances having different Si/Ti ratios, in the same mannes as in Example 1 except for adjusting the amount tetrabutyl orthotitanate. The finally obtained products had Ti/Si ratios of 0.027, 0.023, 0.016, 0.008, and 0.004, and the Si/Ti ratios which were the reciprocal number thereof were 37, 44, 64, 124, and 240. The IR spectra of these samples are shown in FIG. 9. As the Ti content was increased (i.e., as the Si/Ti ratio was decreased) the intensities or extent of the absorption bands of 930 cm$^{-1}$ and 1010 cm$^{-1}$ tend to be increased. Accordingly, it was found that these absorption bands correlated with the Ti content contained in the titanosilicate.

Example 8

Preparation of Layer-Exfoliation Type Titanosilicate Catalyst-3

[Preparation of Ti-MWW (P)]

At 25° C., 14.5 g of PI (mfd. by Wako Pure Chemical Industries Co., Ltd., purity 98%) was dissolved in 30 g of ion-exchanged water to prepare an aqueous PI solution. Under vigorous stirring, 2.3 g of tetrabutylorthotitanate (purity 95%, mfd. by Wako Pure Chemical Industries Co., Ltd.) was added to this aqueous PI solution. The resultant mixture was stirred for 30 minutes to completely promote the hydrolysis of tetrabutylorthotitanate, and thereafter 10 g of the deboronated silicate B having a mole ratio of the boron/silicon of 0.0017 obtained in Example 1 was added thereto, and the stirring was continued for further two hours to obtain a mixture having a mole ratio of 1.SiO$_2$: 0.038.TiO$_2$:1.PI:10.H$_2$O.

This mixture was transferred to a 150 ml-volume Teflon-made autoclave and stirred for 158 hours at a rotation speed of 40 rpm at a temperature of 175° C. After stopping the rotation, the contents were cooled to 25° C. and the solid product was separated from the contents by filtration and washed with ion-exchanged water. The washing was repeated until the pH of the washing water became 9 or less. The thus obtained solid product was dried at a temperature of 80° C., to obtain a layered titanosilicate Ti-MWW(P) as a precursor for an MWW-type zeolite. This layered substance had a titanium/silicon molar ratio of 0.033 and a boron/silicon molar ratio of 0.0019.

[Modification of Ti-MWW (P)]

With respect to 1g of the obtained Ti-MWW (P) solid product, 20 ml of nitric acid of 2 mol/l was added, the solid product was acid-treated at a temperature of 100° C. for 18 hours. The thus acid-treated sample was poured into an aqueous solution which had been obtained by mixing 5.6 g of hexadecyl trimethyl bromide (purity 99%, mfd. by Aldrich Co.), 6.0 g of tetrapropyl ammonium hydroxide (purity 22.5%, an aqueous solution mfd. by Tokyo Kasei Co.), and 12 g of ion-exchanged water. The pH of the resultant slurry was 12.0. The slurry was heated to 80° C. and left standing for 16 hours. Then, the suspension was treated in an ultrasonic irradiation device at 300 W, 35 kHz for one hour, and under stirring, nitric acid of 2 mol/l was added thereto until the pH became 2 or less.

The solid content was collected by centrifugal separation, and further, the solid product was washed with ion-exchanged water. This washing was repeated until the pH of the rinse water became 9 or less. The thus obtained solid product was dried at a temperature of 80° C., and then calcined at a temperature of 600° C. With respect to 1 g of the obtained solid product, 30 ml of nitric acid of 6 mol/l was added thereto to acid-treat the solid product at a temperature of 100° C. for 20 hours. after the acid treatment, the solid obtained by filtration was calcined at a temperature of 600° C. for ten hours. The mole ratio of titanium/silicon of this modified layered substance was 0.024.

Figure 10:
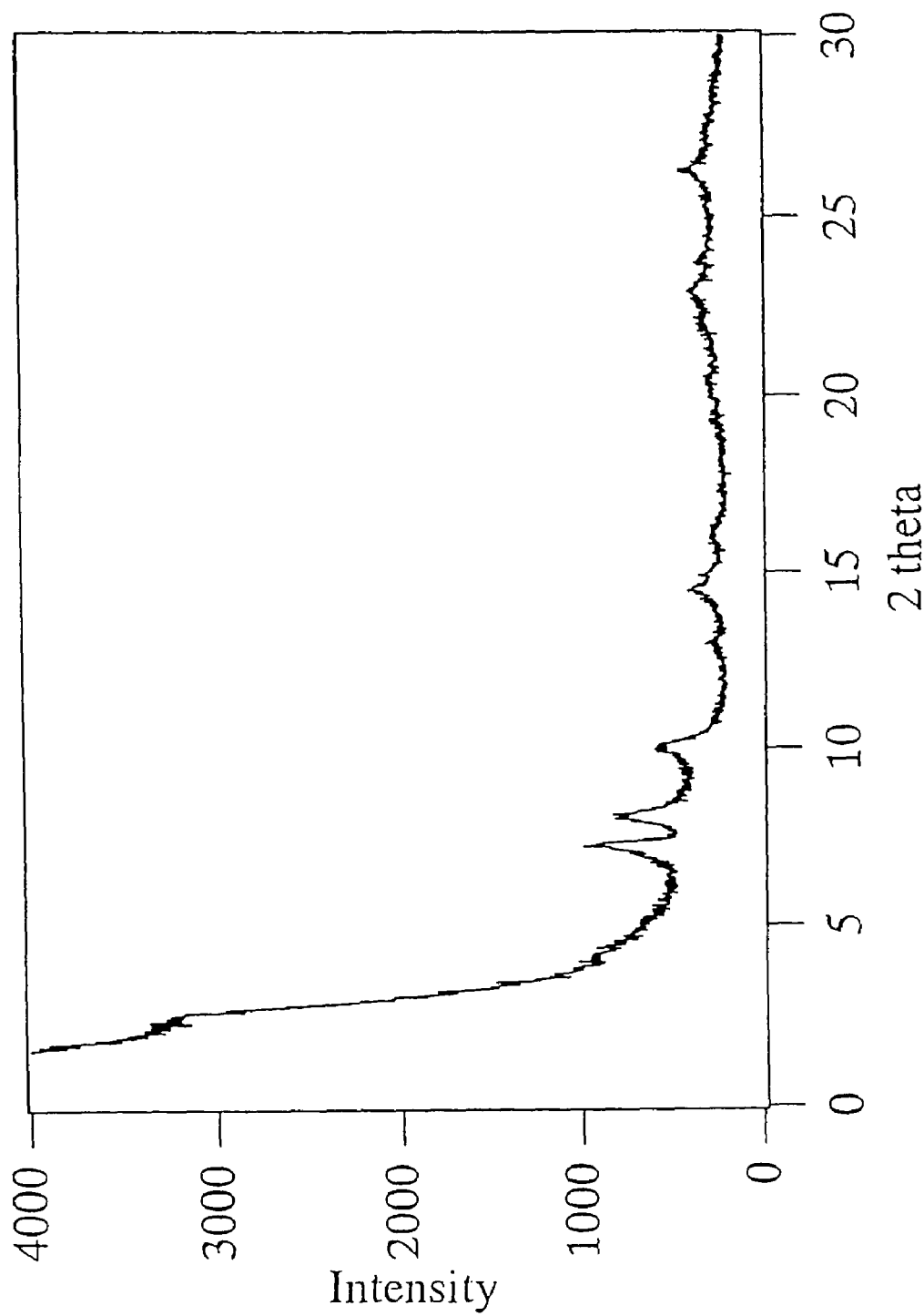
FIG. 10 is an XRD pattern of Catalyst-3 substance obtained in Example 8.
Figure 11:
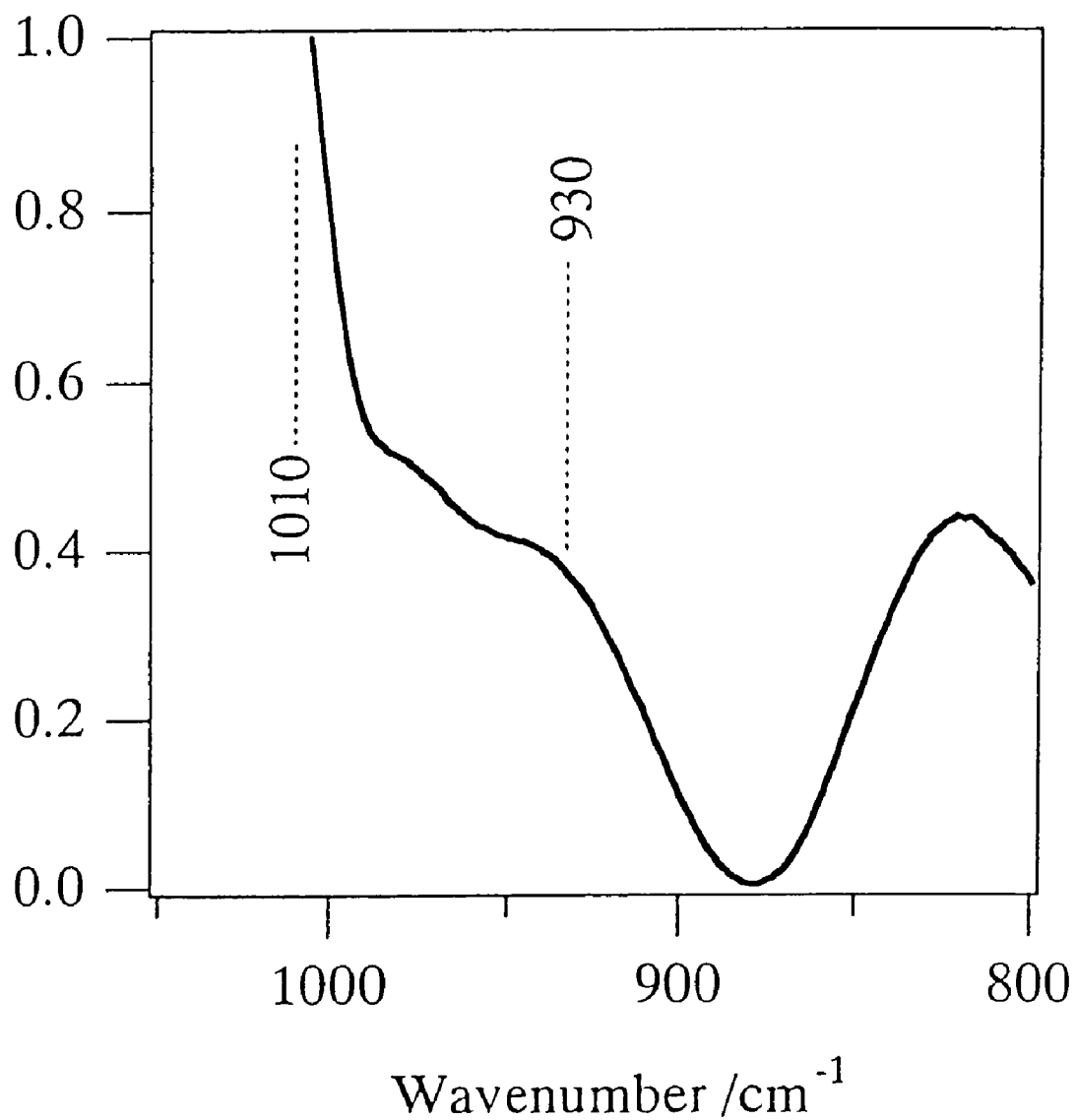
FIG. 11 is an XRD infrared absorption spectrum of Catalyst-3 substance obtained in Example 8.
Figure 12:
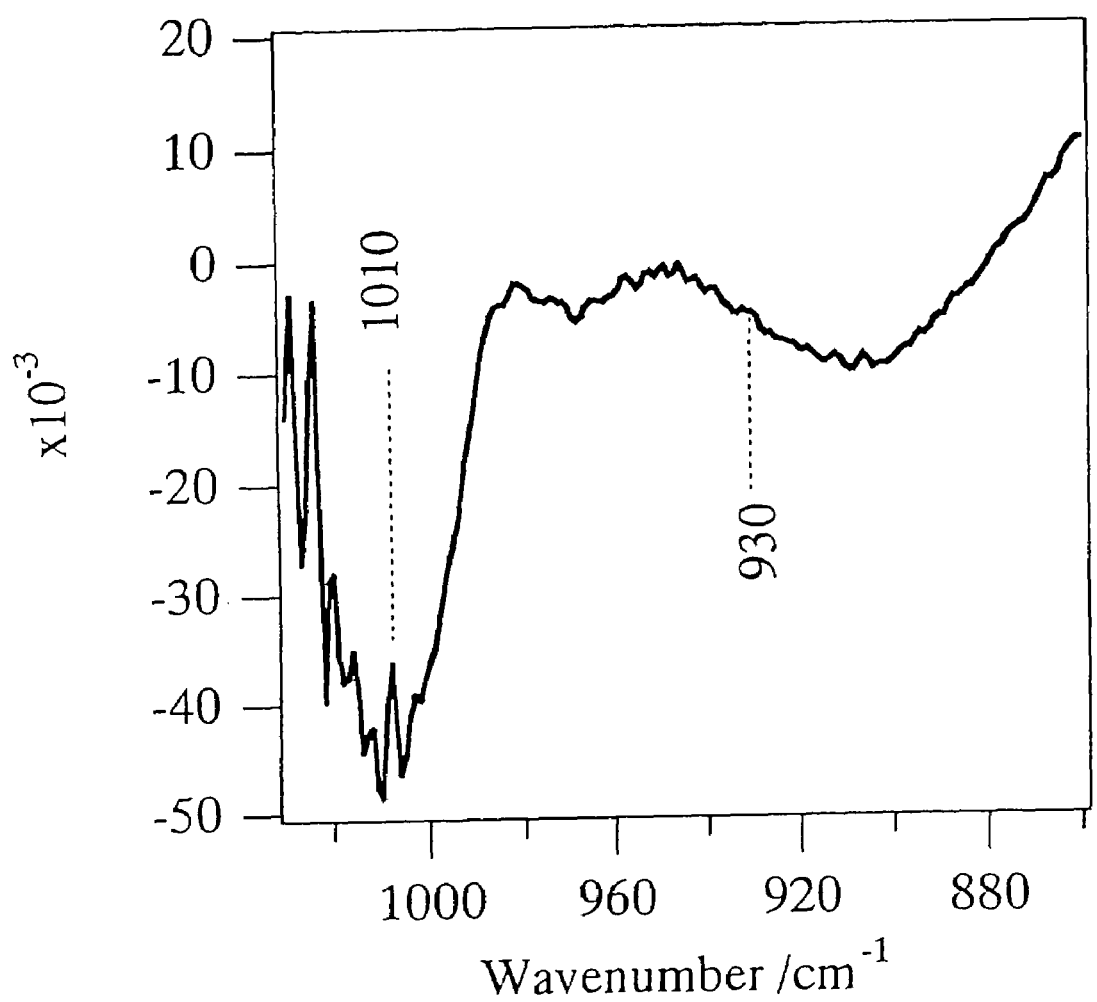
FIG. 12 is the first differential spectrum of FIG. 11.
Figure 13:
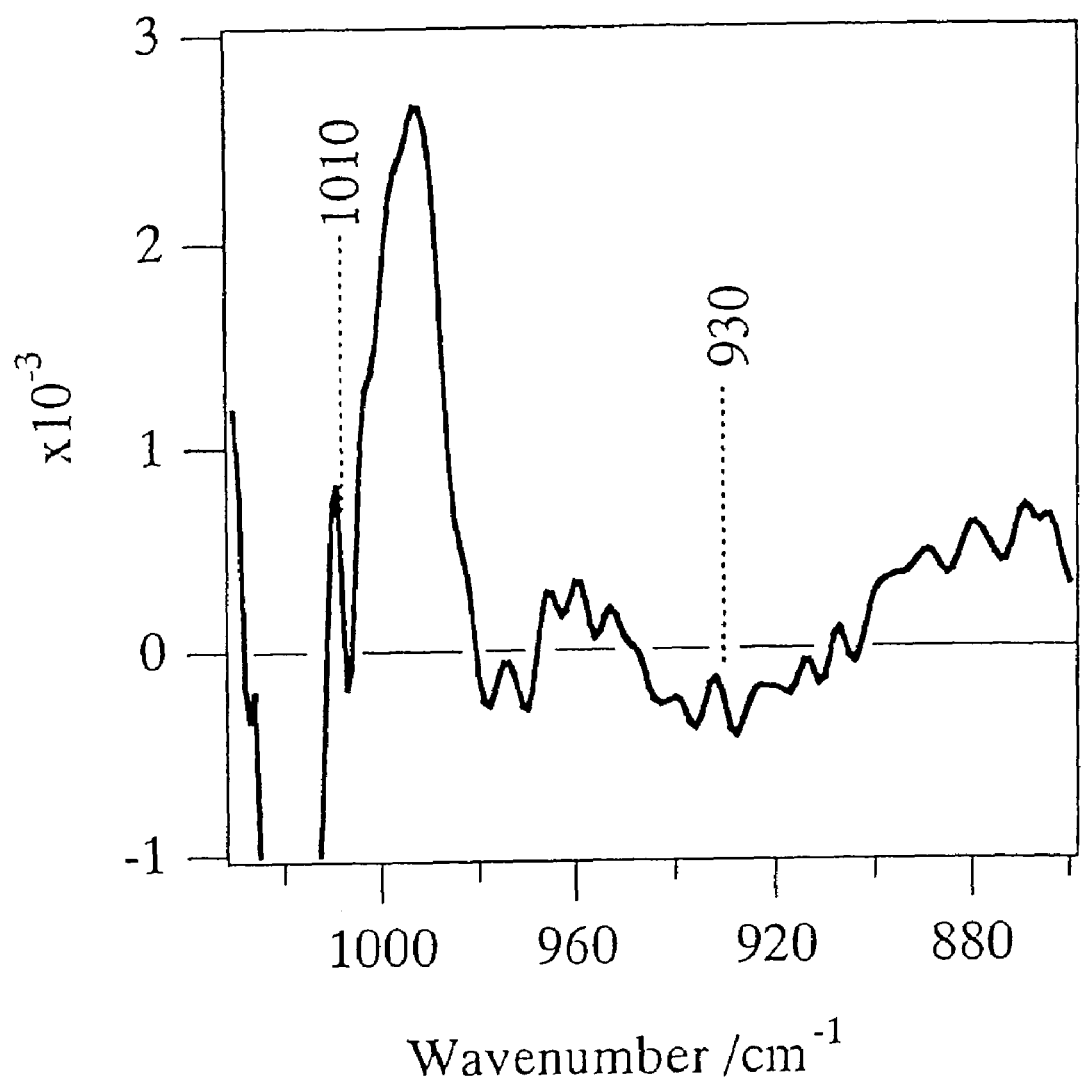
FIG. 13 is the second differential spectrum of FIG. 11.

The XRD pattern of the thus obtained modified layered substance is shown in FIG. 10. This layered substance provides a diffraction pattern similar to that of MWW-type zeolite substance, and therefore it was found that this substance maintains a structure similar to MWW-type structure. In addition, IR absorbance spectrum of this substance is shown in FIG. 11, and the first and second differential spectra thereof are respectively shown in FIGS. 12 and 13. Although it not clear, the curve of the second differential spectrum of FIG. 13 crosses the zero point of the ordinate axis in the neighborhood of at 930 cm$^{-1}$, and there is a local minimum value in the neighborhood of 930 cm$^{-1}$. Accordingly, it was found that this substance had an absorption band having the maximum value in the neighborhood of 930 cm$^{-1}$, as a characteristic of the present invention.

Example 9

Preparation of Layer-Exfoliation Type Titanosilicate Catalyst 4

A modified layered titanosilicate catalyst was obtained in the same manner as in Example 8, except that the irradiation of ultrasonic waves and pH adjustment were not conducted.

The titanium/silicon mole ratio of this modified layered substance was 0.026.

Examples 10-12

The same procedure was repeated in the same manner as in Example 5, except that 10 mg of each of titanosilicate catalysts obtained in Examples 1, 8 and 9 was used, and 0.84 g (10 mmol) of 1-hexene was used. The obtained reaction results are in Table 6. The yield of the intended 1,2-epoxy hexane was respectively 29.3%, 51.8%, and 24.8%. In addition, the turn over number (TON) which had been obtained by dividing the mol number of the product by the mol number of Ti, was respectively 934 mol/mol-Ti, 1390 mol/mol-Ti, and 863 mol/mol-Ti.

acetonitrile, and 0.55 g of 30 mass % (in terms of hydrogen peroxide, 5 mmol) were used. The thus obtained reaction results are shown in Table 6.

Comparative Example 9

The procedure of Example 16 was repeated except that the Comparative catalyst-2, MFI type titanosilicate catalyst obtained in Comparative Example 2 was used. The thus obtained reaction results are shown in Table 6.

TABLE 6

|  | catalyst | substrate | epoxide product | epoxide yield (%)*1 | TON (mol/mol-Ti) |
|---|---|---|---|---|---|
| Example 10 | catalyst 1 | 1-hexene | 1,2-epoxycyclohexane | 29.3 | 934 |
| Example 11 | catalyst 3 | 1-hexene | 1,2-epoxycyclohexane | 51.8 | 1390 |
| Example 12 | catalyst 4 | 1-hexene | 1,2-epoxycyclohexane | 24.8 | 863 |
| Comp. Ex. 7 | comp. catalyst 2 | 1-hexene | 1,2-epoxycyclohexane | 12.0 | 49 |
| Example 13 | catalyst 1 | cyclopentene | cyclopentene oxide | 15.7 | 89 |
| Example 14 | catalyst 3 | cyclopentene | cyclopentene oxide | 58.9 | 306 |
| Example 15 | catalyst 4 | cyclopentene | cyclopentene oxide | 36.0 | 174 |
| Comp. Ex. 8 | comp. catalyst 2 | cyclopentene | cyclopentene oxide | 16.3 | 69 |
| Example 16 | catalyst 1 | cyclooctene | cyclooctene oxide | 4.3 | 24 |
| Example 17 | catalyst 3 | cyclooctene | cyclooctene oxide | 28.2 | 147 |
| Example 18 | catalyst 4 | cyclooctene | cyclooctene oxide | 14.4 | 76 |
| Comp. Ex. 9 | comp. catalyst 2 | cyclooctene | cyclooctene oxide | 1.6 | 7 |
| Example 19 | catalyst 1 | cyclododecene | cyclododecane epoxide | 3.3 | 9 |
| Example 20 | catalyst 3 | cyclododecene | cyclododecane epoxide | 20.7 | 57 |
| Example 21 | catalyst 4 | cyclododecene | cyclododecane epoxide | 16.4 | 40 |
| Comp. Ex. 10 | comp. catalyst 2 | cyclododecene | cyclododecane epoxide | 1.2 | 3 |

*1epoxide yield: (amount of epoxide produced) (mol)/(amount of raw material hydrogen peroxide) (mol) × 100 (%)

Comparative Example 7

The procedure of Example 10 was repeated except that 25 mg of the Comparative catalyst, MFI type titanosilicate catalyst obtained in Comparative Example 2 was used, and 0.42 g of 1-hexene (5 mmol), 3.9 g (5 ml) of acetonitrile, and 0.55 g of 30 mass % (in terms of hydrogen peroxide, 5 mmol) were used. The thus obtained reaction results are shown in Table 6.

Example 13-15

The procedure of Example 10 was repeated except that 25 mg of each of the titanosilicate catalysts obtained in Examples 1, 8 and 9 was used, and 0.34 g (5 mmol) of cyclopentene, 3.9 g (5 ml) of acetonitrile, and 0.55 g of 30 mass % (in terms of hydrogen peroxide, 5 mmol) were used; and the reaction was started when the temperature of the reaction mixture reached 37° C. in a water bath of 40° C. The thus obtained reaction results are shown in Table 6.

Comparative Example 8

The procedure Examples 13 was repeated except that the Comparative catalyst-2, MFI type titanosilicate catalyst obtained in Comparative Example 2 was used. The thus obtained reaction results are shown in Table 6.

Examples 16-18

The procedure of each of Examples 10-12 was repeated except that 0.55 g (5 mmol) of cyclooctene, 7.8 g (10 ml) of

Examples 19-21

The procedure of each of Examples 10-12 was repeated except that 0.42 g (2.5 mmol) of cyclododecen, and 0.275 g of 30 mass % of hydrogen peroxide (in terms of hydrogen peroxide, 2.5 mmol) were used. The thus obtained reaction results are shown in Table 6.

Comparative Example 10

The procedure of Example 19 was repeated except that the Comparative catalyst-2, MFI type titanosilicate catalyst obtained in Comparative Example 2 was used. The thus obtained reaction results are shown in Table 6.

Example 22

The MWW-type titanosilicate catalyst 1 (10 mg) obtained in Example 1 was charged in a 30 ml-autoclave equipped with a magnetic stirrer, and 7.8 g (10 ml) of acetonitrile, 1.1 g of 30 wt. % of aqueous hydrogen peroxide solution (in terms of hydrogen peroxide, 10 m mol) were added thereto. After the resultant reaction system was cooled, the air in the autoclave was evacuated with vacuum pump. Then, under stirring with the magnetic stirrer, the autoclave was heated in a water bath of 40° C., and propylene was supplied to the autoclave by connecting the autoclave with a propylene gas cylinder equipped with a pressure controller and the internal pressure in the autoclave was maintained at 0.25 MPa. One hour after, the supply of propylene gas was stopped, the gaseous product in the autoclave was trapped by bubbling the gaseous product in 10 ml of acetonitrile, and then the suspension in autoclave was added to this trap liquid to collect all of the product. Then, the catalyst was separated by a centrifugal separation device, and the concentration of organic substances in the thus obtained reaction liquid was analyzed by gas chromatography. Further, the concentration of the unreacted hydrogen peroxide was determined by potentiometric titration using Ce (IV). It was found that 6.00 mmol of propylene glycol and 0.003 mmol of propylene oxide were produced, and the selectivities thereof were respectively 99.95% and 0.05%. In addition, in addition, the conversion of hydrogen peroxide was 67.4%, and the efficiency of the hydrogen peroxide was 85.1%.

Comparative Example 11

Propylene was oxidized in the same manner as in Example 22 was repeated except that the Comparative catalyst-1 obtained in Comparative Example 1 was used. It was found that 3.04 mmol of propylene oxide and 0.005 mmol of propylene glycol were produced, and the selectivities thereof were respectively 99.8% and 0.2%. In addition, in addition, the conversion of hydrogen peroxide was 44.6%, and the efficiency of the hydrogen peroxide was 69.5%.

Comparative Example 12

Propylene was oxidized in the same manner as in Example 22 was repeated except that the Comparative catalyst-2 obtained in Comparative Example 2 was used. It was found that 0.32 mmol of propylene oxide and 0.004 mmol of propylene glycol were produced, and the selectivities thereof were respectively 98.7% and 1.3%. In addition, in addition, the conversion of hydrogen peroxide was 8.3%, and the efficiency of the hydrogen peroxide was 39.6%.

INDUSTRIAL APPLICABILITY

As described in the foregoing pages, it is apparent that the titanosilicate catalyst of the present invention, represented by the following compositional formula (I) and characterized by the infrared absorption spectrum measured in the dehydrated state, where on the spectrum, an absorption band having a relative maximum value at 930±15 cm$^{-1}$ is observed, is a very useful catalyst for use in the production of an oxidized compound of an oxide compound using a peroxide as the oxidizing agent.

$xTiO_2 \cdot (1-X)SiO_2$     Compositional Formula (1)

(wherein x is from 0.0001 to 0.2).

It is also clear that according to the production process of the titanosilicate catalyst of present invention, a high-performance titanosilicate catalyst can be obtained with good efficiency.

The invention claimed is:

1. A titanosilicate represented by the following compositional formula (1), wherein in the infrared absorption spectrum measured in the dehydrated state, the absorption spectrum has an absorption band having a relative maximum value at 930±15 cm$^{-1}$:

$xTiO_2 \cdot (1-x)SiO_2$     Compositional Formula (1)

(wherein x is from 0.0001 to 0.2), and
wherein in the infrared absorption spectrum measured in the dehydrated state, the greatest value in the region of 900-950 cm$^{-1}$ of the absorption spectrum is present in the region of 930±15 cm$^{-1}$.

2. The titanosilicate according to claim 1, wherein in the infrared absorption spectrum measured in the dehydrated state, the greatest value in the region of 900-950 cm$^{-1}$ of the absorption spectrum is present in the region of 930±10 cm$^{-1}$.

3. The titanosilicate according to claim 1, wherein in the infrared absorption spectrum measured in the dehydrated state, the absorption spectrum has an absorption band having a relative maximum value at 1010±15 cm$^{-1}$ in addition to 930±15 cm$^{-1}$.

4. The titanosilicate according to claim 3, wherein in the infrared absorption spectrum measured in the dehydrated state, the absorption spectrum has an absorption band having a relative maximum value at 865+15 cm$^{-1}$ in addition to 930±15 cm$^{-1}$.

5. The titanosilicate according to claim 1, which is a crystalline titanosilicate having a structure code MWW characterized by the powder X-ray diffraction pattern shown in Table 7:

TABLE 7

| Powder X-Ray Diffraction Lines provided by MWW Structure | |
|---|---|
| d/Å | Relative Intensity (s: strong, m: medium, w: weak) |
| 12.3 ± 0.6 | s |
| 11.0 ± 0.6 | s |
| 8.8 ± 0.5 | s |
| 6.2 ± 0.4 | m |
| 5.5 ± 0.3 | w |
| 3.9 ± 0.2 | m |
| 3.7 ± 0.2 | w |
| 3.4 ± 0.2 | s |

(in the above Table, "d/Å" means that the unit of the lattice spacing d is Angstrom.)

6. The titanosilicate according to claim 1, wherein x is from 0.001 to 0.2.

7. A process for producing the titanosilicate described in claim 1, comprising the following first to fourth steps:
First Step:
a step of heating a mixture containing a template compound, a boron-containing compound, a silicon-containing compound and water to obtain a precursor (A);
Second Step:
a step of acid-treating the precursor (A) obtained in the first step;
Third Step:
a step of heating the acid-treated precursor (A) obtained in the second step together with a mixture containing a template compound, a titanium-containing compound and water to obtain a precursor (B); and
Fourth Step:
a step of calcining the precursor (B) obtained in the third step to obtain the titanosilicate.

8. The process for producing the titanosilicate according to claim 7, wherein the following first-2 step is performed between the first step and the second step and the substance obtained in the first-2 step is used instead of the precursor (A) in the second step:
First-2 Step:
a step of calcining a part or entirety of the precursor (A) obtained in the first step.

9. The process for producing the titanosilicate according to claims 8, wherein the calcination temperature in the first-2 step is from 200 to 700° C.

10. The process for producing the titanosilicate according to claim 7, wherein the following third-2 step is performed between the third step and the fourth step and the substance obtained in the third-2 step is used instead of the precursor (B) in the fourth step:

Third-2 Step:
  a step of acid-treating a part or entirety of the precursor (B) obtained in the third step.

11. The process for producing the titanosilicate according to claims 7, wherein the following third-3 step is performed between the third step or third-2 step, and the fourth step, and the substance obtained in the third-3 step is used instead of the precursor (B) in the fourth step:

Third-3 Step:
  a step of heating the precursor (B) obtained in the third step, or the acid-treated precursor (B) obtained in the third-2 step, in the presence of a swelling agent so as to swell the layered precursor, to thereby modify the state of the superposition thereof.

12. The process for producing the titanosilicate according to claim 7, wherein the template compound is a nitrogen-containing compound.

13. The process for producing the titanosilicate according to claim 12, wherein the nitrogen-containing compound is amine and/or quaternary ammonium compound.

14. The process for producing the zeolite substance according to claim 12, wherein the nitrogen-containing compound is at least one member selected from the group consisting of piperidine, hexamethyleneimine and a mixture thereof.

15. The process for producing the titanosilicate according to claims 7, wherein the boron-containing compound is at least one member selected from the group consisting of boric acid, borate, boron oxide, boron halide and trialkyl-borons.

16. The process for producing the titanosilicate according to claim 7, wherein the silicon-containing compound is at least one member selected from the group consisting of silicic acid, silicate, silicon oxide, silicon halide, fumed silicas, tetraalkyl orthosilicates and colloidal silica.

17. The process for producing the titanosilicate according to claim 7, wherein the ratio of boron to silicon in the mixture at the first step is, in terms of the molar ratio, boron:silicon=0.01 to 10:1.

18. The process for producing the titanosilicate according to claim 7, wherein the ratio of boron to silicon in the mixture at the first step is, in terms of the molar ratio, boron:silicon=0.05 to 10:1.

19. The process for producing the titanosilicate according to claim 7, wherein the ratio of water to silicon in the mixture at the first step is, in terms of the molar ratio: water:silicon=5 to 200:1.

20. The process for producing the titanosilicate according to claim 7, wherein the ratio of template compound to silicon in the mixture.

21. The process for producing the titanosilicate according to claim 7, wherein the heating temperature in the first step is from 110 to 200° C.

22. The process for producing the titanosilicate according to claim 7, wherein the acid used for the acid-treatment in the second step is a nitric acid or a sulfuric acid.

23. The process for producing the titanosilicate according to claim 7, wherein the heating temperature in the third step is from 110 to 200° C.

24. The process for producing the titanosilicate according to claim 7, wherein the calcination temperature in the fourth step is from 200 to 700° C.

25. The process for producing the titanosilicate according to claim 7, wherein in the third step, the acid-treated precursor (A) obtained in the second step and the mixture containing a template compound, a titanium-containing compound and water are previously mixed and then heated.

26. The process for producing the titanosilicate according to claim 7, wherein in the third step, the acid-treated precursor (A) is treated by a dry gel method such that a mixture containing the acid-treated precursor (A) obtained in the second step, a titanium-containing compound and water and a mixture containing a template compound and water are charged separately, the vapor of the containing a template compound and water is caused to contact the mixture containing the titanium-containing compound and the acid-treated precursor (A).

27. A process for producing an oxidized compound, comprising performing an oxidation reaction of an organic compound using the oxidizing agent in the presence of the titanosilicate described in claim 1.

28. The process for producing an oxidized compound according to claim 27, wherein the oxidizing agent is oxygen or peroxide.

29. The process for producing an oxidized compound according to claim 28, wherein the peroxide is at least one compound selected from the group consisting of hydrogen peroxide, tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, ethylnaphthalene hydroperoxide and peracetic acid.

30. The process for producing an oxidized compound according to claim 27, wherein the oxidation reaction is performed in the presence of at least one solvent selected from the group consisting of alcohols, ketones, nitriles and water.

31. The process for producing an oxidized compound according to claim 27 wherein the oxidation reaction of an organic compound is an oxidation reaction of a carbon-carbon double bond.

32. The process for producing an oxidized compound according to claim 27, wherein the oxidation reaction of an organic compound is an epoxidation reaction or a diolation reaction.

33. The process for producing an oxidized compound according to claim 27, wherein the oxidation reaction of an organic compound is an ammoximation.

\* \* \* \* \*